(12) United States Patent
Heaton, II et al.

(10) Patent No.: US 8,798,700 B1
(45) Date of Patent: Aug. 5, 2014

(54) OXIMETER WITH MARKING FEATURE

(75) Inventors: Larry C. Heaton, II, Pleasanton, CA (US); Robert E. Lash, Redwood City, CA (US)

(73) Assignee: ViOptix, Inc., Fremont, CA (US)

( * ) Notice: Subject to any disclaimer, the term of this patent is extended or adjusted under 35 U.S.C. 154(b) by 1712 days.

(21) Appl. No.: 12/178,359

(22) Filed: Jul. 23, 2008

(51) Int. Cl.
*A61B 5/00* (2006.01)

(52) U.S. Cl.
USPC .......................................................... 600/323

(58) Field of Classification Search
USPC .................. 600/309, 310, 322, 323; 606/116
See application file for complete search history.

(56) References Cited

U.S. PATENT DOCUMENTS

| | | | |
|---|---|---|---|
| 4,286,599 A * | 9/1981 | Hahn et al. | ..................... 606/116 |
| 5,088,493 A | 2/1992 | Giannini et al. | |
| 6,078,833 A | 6/2000 | Hueber | |
| 6,285,904 B1 | 9/2001 | Weber et al. | |
| 6,516,209 B2 | 2/2003 | Cheng et al. | |
| 6,549,284 B1 | 4/2003 | Boas et al. | |
| 6,587,703 B2 | 7/2003 | Cheng et al. | |
| 6,597,931 B1 | 7/2003 | Cheng et al. | |
| 6,708,048 B1 | 3/2004 | Chance | |
| 6,735,458 B2 | 5/2004 | Cheng et al. | |
| 7,247,142 B1 | 7/2007 | Elmandjra et al. | |
| 7,254,427 B2 | 8/2007 | Cho et al. | |
| D567,949 S | 4/2008 | Lash et al. | |
| 7,355,688 B2 | 4/2008 | Lash et al. | |
| D568,479 S | 5/2008 | Mao et al. | |
| 2004/0111016 A1 | 6/2004 | Casscells et al. | |
| 2008/0181715 A1 * | 7/2008 | Cohen | ........................... 401/232 |

OTHER PUBLICATIONS

Hueber, Dennis et al., "New Optical Probe Designs for Absolute (Self-Calibrating) NIR Tissue Hemoglobin Measurements," in Proceedings of Optical Tomography and Spectroscopy of Tissue III, vol. 3597, 618-631(Jan. 1999).

* cited by examiner

*Primary Examiner* — Max Hindenburg
*Assistant Examiner* — Jonathan M Foreman
(74) *Attorney, Agent, or Firm* — Aka Chan LLP

(57) ABSTRACT

A medical device such as an oximeter includes a marking feature. In an implementation, a marking mechanism of the device marks tissue based on a location of where a measurement was taken by the device. In an implementation, the marking mechanism of the device marks tissue based on an oxygen saturation measurement obtained by the device.

26 Claims, 13 Drawing Sheets

Drop    Spray    Stamp

OXIMETER WITH MARKING FEATURE

BACKGROUND OF THE INVENTION

The present invention relates to the field of medical devices, and more specifically to an oximeter or other medical device having a marking feature.

Medical devices are among the marvels of modern medicine. Doctors and people use instruments to help diagnose and treat medical conditions and assist in medical and other procedures. Some revolutionary medical devices include the balloon catheter, oximeter, stent, and shunt. Over the years, these have improved the lives of many millions of people—allowing them to live better, longer, and more fulfilling lives.

Medical devices continue to evolve and improve. Today's medical devices are more accurate, effective, and easier to use than those introduced just a few years ago. Many types of medical devices are even sold for people to use at home. Some common medical devices used by people at home are for monitoring blood pressure, blood glucose, fertility, body temperature (instantly and accurately), and body fat percentage.

Despite the widespread success of current medical devices, there is a need for new and improved medical devices that provide greater features and functionality, and devices which generally help improve the lives of human beings.

Oximeters are medical devices used to measure oxygen saturation of tissue in patients. Typically, an oximeter takes a measurement at a single location. For some medical procedures, it is important to obtain oxygen saturation readings at numerous positions or points across an area of tissue.

A doctor can use an oximeter to spot check multiple locations. For example, to make two successive measurements, the doctor will place a sensor at a first location and make a first measurement, and then move the sensor to a second location to make a second measurement. Any number of measurements may be made using this spot-checking approach across a tissue surface.

Using such an approach, the doctor will have to take and remember the readings at multiple positions across the tissue region. The number of readings may be large. The process of remembering where measurements were taken and what the measurements were at those points may become inefficient and burdensome during any procedure, especially when a patient is in critical condition.

For example, when transplanting tissue, a doctor needs oxygen saturation measurements at multiple points of the tissue to ensure blood flow (carrying fresh oxygen) is uniform throughout the tissue region. The doctor will have to remember the readings taken at multiple positions across the tissue region. Based on these readings, the doctor will make adjustments as needed (e.g., alter how blood vessels are connected). Otherwise, portions of the tissue not receiving sufficient oxygen flow will eventually die.

Therefore, an oximeter with a marking feature is needed. It is desirable that an oximeter indicate where measurements have been made and what oxygen saturation measurements are at different positions of a tissue area.

BRIEF SUMMARY OF THE INVENTION

A medical device such as an oximeter includes a marking feature. In an implementation, a marking mechanism of the device marks tissue based on a location of where a measurement was made by the device. In an implementation, the marking mechanism of the device marks tissue based on a measurement obtained by the device.

By using an oximeter with a marking feature, a doctor can mark a tissue surface in such a way that the mark reveals the oxygen saturation level at that point. Thus, the device will mark multiple points of the same tissue immediately after taking each oxygen saturation measurement and build a visual map of the tissue's viability. The doctor can then more easily reference the points of the tissue at which oxygen saturation measurements were taken and compare them in order to make a more accurate decision regarding the patient's treatment.

An oximeter with a marking feature gives doctors greater access to information relating to a patient's tissue health. For example, tissue viability is an important concern during surgery. By using a tissue oximeter with a marking feature, a doctor can immediately view local oxygen and blood circulation during the procedure.

A marking feature enhances the efficacy of tissue oximeters as it enables doctors and other medical professionals to indicate the specific location where a measurement was taken. Furthermore, medical professionals can increase efficiency within the health care field by allowing the oxygen saturation of various points throughout a particular tissue to be immediately visible. A doctor can see the oxygen saturation of a particular tissue just by looking at the markings on the tissue surface instead of repeatedly taking measurements.

In an implementation, a probe for a medical device includes: a cable interface, the cable interface being adapted to allow the probe to be connected to a first radiation emitter and a first photodetector, where the first radiation emitter and the first photodetector are external to the probe. There is a sensor unit including a first source structure and a first detector structure. The first source structure is arranged to be connected to the first radiation emitter via the cable interface. The first detector structure is arranged to be connected to the first photodetector via the cable interface. There is a marking mechanism output which positioned closer to the first detector structure than the cable interface.

In a specific implementation, the sensor unit includes a second source structure and a second detector structure. The second source structure is arranged to be connected to a second radiation emitter via the cable interface. The second detector structure is arranged to be connected to a second photodetector via the cable interface, where the second radiation emitter and the second photodetector are external to the probe.

A first distance is between the first source structure and the first detector structure. A second distance is between the first source structure and the second detector structure. A third distance is between the second source structure and the first detector structure. A fourth distance is between the second source structure and the second detector structure. The first distance is not equal to the fourth distance and the second distance is not equal to the third distance.

In various implementations, the marking mechanism output includes an ink nozzle. The marking mechanism output is positioned within ten millimeters of the first detector structure. The marking mechanism output is positioned within nine millimeters of the first detector structure. The marking mechanism output is positioned within eight millimeters of the first detector structure. The marking mechanism output is positioned within seven millimeters of the first detector structure. The marking mechanism output is positioned within six millimeters of the first detector structure. The marking mechanism output is positioned within five millimeters of the first detector structure. The marking mechanism output is positioned within four millimeters of the first detector structure. The marking mechanism output is positioned within three millimeters of the first detector structure. The marking mechanism output is positioned within two millimeters of the first detector structure.

Further, the marking mechanism output is connected to the sensor unit. The probe includes a handle, where the sensor unit is connected to the handle, and a light emitting diode, also connected to a handle. The marking mechanism output can also be connected to the handle.

In an implementation, a probe of a medical device includes: a first retaining mechanism, to removably connect a sensor unit to the probe; a first marking reservoir; a second retaining mechanism, to connect the first marking reservoir to the probe; and a marking mechanism, connected to the first marking reservoir.

In a specific implementation, the second retaining mechanism removably connects the first marking reservoir to the probe. In this implementation, the marking reservoir is user replaceable, just as the sensor is user replaceable.

The second retaining mechanism can be internal to the probe, such as held within or in a compartment of the probe. The first marking reservoir can have a transparent or see-through window, so the user can see how much ink or other material is left.

The probe typically also includes an elongated handle, which a user can grasp. The first marking reservoir, the second retaining mechanism, and the marking mechanism are connected to this handle.

The first marking reservoir includes a first ink of a first color and the probe further includes: a second marking reservoir including a second ink of a second color, different from the first, where the second marking reservoir is coupled to the marking mechanism. A third retaining mechanism connects the second marking reservoir to the probe.

In a specific implementation, a method includes: transmitting a first light through a source structure into a target tissue; receiving a second light transmitted through the target tissue at a detector structure; based on values for the first and second light, determining an oxygen saturation value for the target tissue; and after the determining an oxygen saturation value, marking a tissue surface representative of a location of the target tissue.

Marking a tissue surface can include placing ink on the tissue surface. However, if the determining an oxygen saturation value does not successfully obtain a result, the tissue surface is not marked. After the determining an oxygen saturation value, the above method can further include turning on a light indicator at the probe.

In a specific implementation, a method includes: transmitting a first light through a source structure into a target tissue; receiving a second light transmitted through the target tissue at a detector structure; based on values for the first and second light, determining an oxygen saturation value for the target tissue; and after the determining an oxygen saturation value, marking a tissue surface representative of the oxygen saturation value.

The marking a tissue surface can include: when the oxygen saturation value is below a first threshold value, not marking the tissue surface; and when the oxygen saturation value is above the first threshold value, marking the tissue surface with a mark. The marking a tissue surface can include: when the oxygen saturation value is below a first threshold value, marking the tissue surface with a first mark having a first characteristic; and when the oxygen saturation value is above the first threshold value, marking the tissue surface with a second mark having a second characteristic.

The marking a tissue surface can further include: when the oxygen saturation value is above a second threshold value (where the second threshold value is above the first threshold value), marking the tissue surface with a third mark having a third characteristic. In an implementation, the first mark is an ink of a first color, the second mark is an ink of a second color, and the third mark is an ink of a third color. The first, second, and third colors are visually distinguishable from each other.

In various implementations, the method further includes: when the oxygen saturation value is below the first threshold value, not turning on a light indicator used specially for a warning purpose and, when the oxygen saturation value is above the first threshold value, turning on the light indicator. A variation of this method further includes: when the oxygen saturation value is below the first threshold value, turning on a first light indicator having a first characteristic; and when the oxygen saturation value is above the first threshold value, turning on a second light indicator having a second characteristic.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
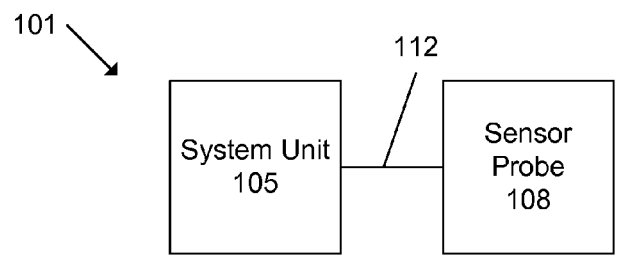
FIG. 1 shows a block diagram of an oximeter system for measuring oxygen saturation of tissue in a patient.

FIG. 1 shows an oximeter system 101 for measuring oxygen saturation of tissue in a patient. The system includes a system unit 105 and a sensor probe 108, which is connected to the system unit via a wired connection 112. Connection 112 may be an electrical, optical, or another wired connection including any number of wires (e.g., one, two, three, four, five, six, or more wires or optical fibers), or any combination of these or other types of connections. In other implementations of the invention, however, connection 112 may be wireless such as via a radio frequency (RF) or infrared communication.

Typically, the system is used by placing the sensor probe in contact or close proximity to tissue (e.g., skin or nerve) at a site where an oxygen saturation or other related measurement is desired. The system unit causes an input signal to be emitted by the sensor probe into the tissue (e.g., human tissue). There may be multiple input signals, and these signals may have varying or different wavelengths. The input signal is transmitted into or through the tissue.

Then, after transmission through or reflection off the tissue, the signal is received at the sensor probe. This received signal is received and analyzed by the system unit. Based on the received signal, the system unit determines the oxygen saturation of the tissue and displays a value on a display of the system unit.

In an implementation, the system is a tissue oximeter, which can measure oxygen saturation without requiring a pulse or heart beat. A tissue oximeter of the invention is applicable to many areas of medicine and surgery including plastic surgery and spinal surgery. The tissue oximeter can make oxygen saturation measurements of tissue where there is no pulse; such tissue, for example, may have been separated from the body (e.g., a flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbances of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. These patents are assigned to the same assignee as this patent application and are incorporated by reference.

Figure 2:
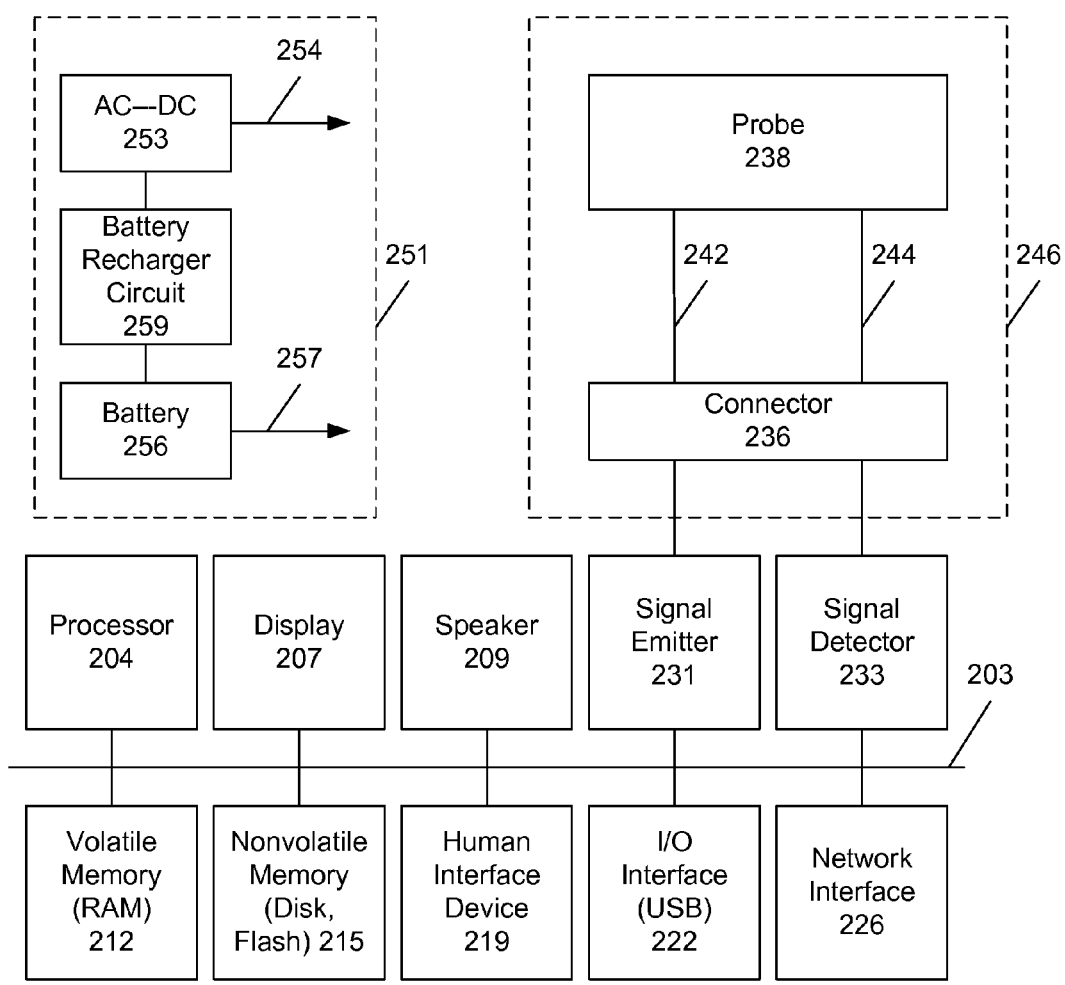
FIG. 2 shows a more detailed block diagram of a specific implementation of the system of FIG. 1.

FIG. 2 shows greater detail of a specific implementation of the system of FIG. 1. The system includes a processor 204, display 207, speaker 209, signal emitter 231, signal detector 233, volatile memory 212, nonvolatile memory 215, human interface device or HID 219, I/O interface 222, and network interface 226. These components are housed within a system unit enclosure. Different implementations of the system may include any number of the components described, in any combination or configuration, and may also include other components not shown.

The components are linked together using a bus 203, which represents the system bus architecture of the system. Although this figure shows one bus that connects to each component, the busing is illustrative of any interconnection scheme serving to link the subsystems. For example, speaker 209 could be connected to the other subsystems through a port or have an internal direct connection to processor 204.

A sensor probe 246 of the system includes a probe 238 and connector 236. The probe is connected to the connector using wires 242 and 244. The connector removably connects the probe and its wires to the signal emitter and signal detectors in the system unit. There is one cable or set of cables 242 to connect to the signal emitter, and one cable or set of cables 244 to connect to the signal detector. In an implementation the cables are fiber optic cables, but in other implementations, the cables are electrical wires.

Signal emitter 231 is a light source that emits light at one or more specific wavelengths. In a specific implementation, two wavelengths of light (e.g., 690 nanometers and 830 nanometers) are used. In other implementations, other wavelengths of light may be used. The signal emitter is typically implemented using a laser diode or light emitting diode (LED). Signal detector 233 is typically a photodetector capable of detecting the light at the wavelengths produced by the signal emitter.

The connector may have a locking feature; e.g., insert connector, and then twist or screw to lock. If so, the connector is more securely held to the system unit and it will need to be unlocked before it can be removed. This will help prevent accidental removal of the probe.

The connector may also have a first keying feature, so that the connector can only be inserted into a connector receptacle of the system unit in one or more specific orientations. This will ensure that proper connections are made.

The connector may also have a second keying feature that provides an indication to the system unit which type of probe is attached. The system unit may handle making measurements for a number of different types of probes. When a probe is inserted, the system uses the second keying feature to determine which type of probe is connected to the system. Then the system can perform the appropriate functions, use the proper algorithms, or otherwise make adjustments in its operation for the specific probe type.

For example, when the system detects a cerebral probe is connected, the system uses cerebral probe algorithms and operation. When the system detects a thenar probe is connected, the system uses thenar probe algorithms and operation. A system can handle any number of different types of probes. There may be different probes for measuring different parts of the body, or different sizes or versions of a probe for measuring a part of the body (e.g., three different thenar probe models).

With the second keying feature, the system will be able to distinguish between the different probes. The second keying feature can use any type of coding system to represent each probe including binary coding. For example, for a probe, there are four second keying inputs, each of which can be a logic 0 or 1. With four second keying inputs, the system will be able to distinguish between sixteen different probes.

Typically, probe 246 is a handheld tool and a user moves the probe from one point to another to make measurements. However, in some applications, probe 246 is part of an endoscopic instrument or robotic instrument, or both. For example, the probe is moved or operated using a guiding interface, which may or may not include haptic technology.

In various implementations, the system is powered using a wall outlet or battery powered, or both. Block 251 shows a power block of the system having both AC and battery power options. In an implementation, the system includes an AC-DC converter 253. The converter takes AC power from a wall socket, converts AC power to DC power, and the DC output is connected to the components of the system needing power (indicated by an arrow 254). In an implementation, the system is battery operated. The DC output of a battery 256 is connected to the components of the system needing power (indicated by an arrow 257). The battery is recharged using a recharger circuit 259, which received DC power from an AC-DC converter. The AC-DC converter and recharger circuit may be combined into a single circuit.

The nonvolatile memory may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

The processor may include multiple processors or a multicore processor, which may permit parallel processing of information. Further, the system may also be part of a distributed environment. In a distributed environment, individual systems are connected to a network and are available to lend resources to another system in the network as needed. For example, a single system unit may be used to collect results from numerous sensor probes at different locations.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, Matlab (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows CE, Windows Mobile), Linux, HP-UX, UNIX, Sun OS, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may interface to other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or other device (e.g., laptop computer, smartphone, or personal digital assistant), a user accesses a system of the invention through a network such as the Internet. The user will be able to see the data being gathered by the machine. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 3:
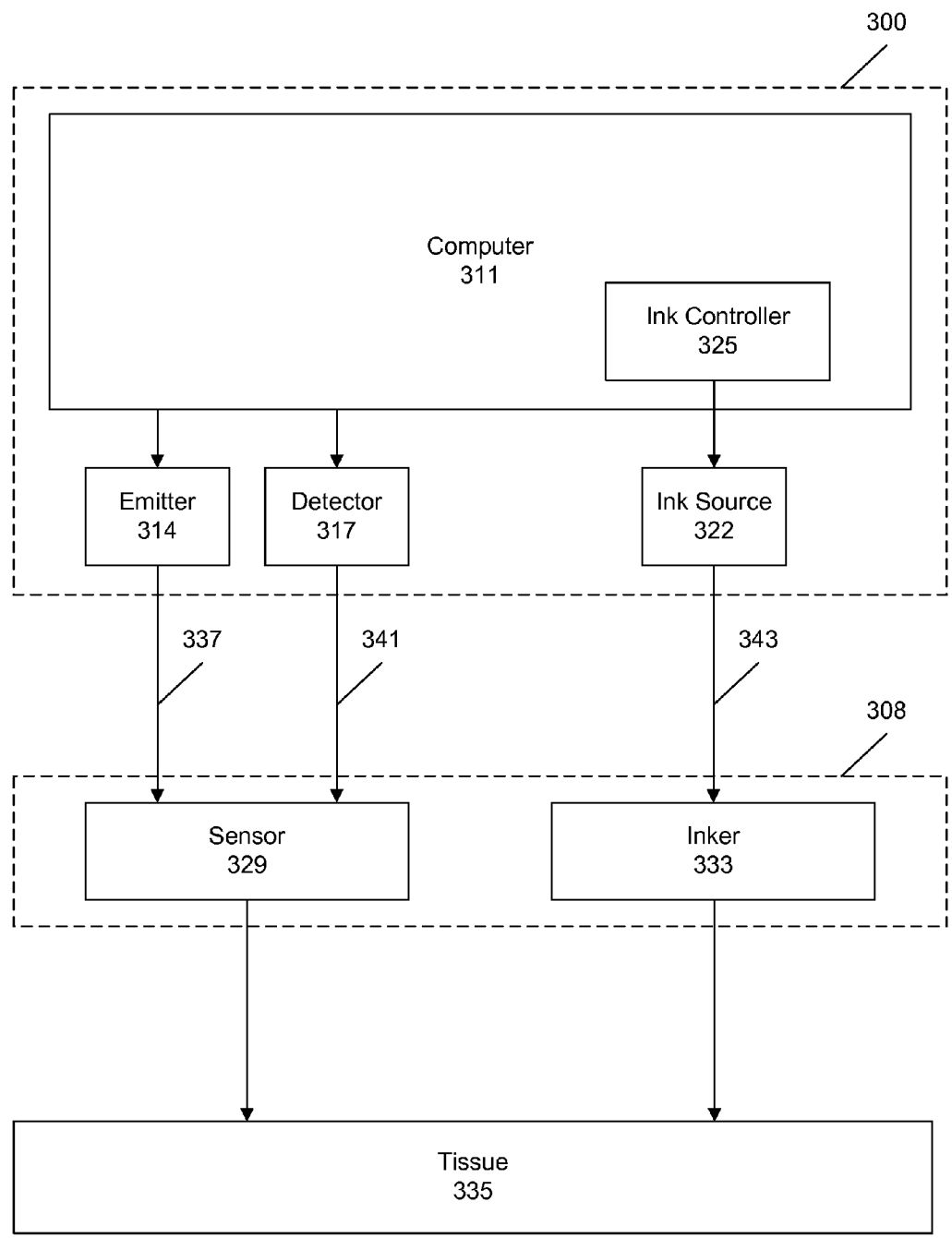
FIG. 3 shows a block diagram of an oximeter system incorporating a marking feature.

FIG. 3 shows a block diagram of a specific implementation of a system of the invention. This system can measure oxygen saturation of tissue and also mark a location of where the measurement was made using a marking mechanism. This implementation includes a system console (or enclosure) 300 and a probe 308. Typically, the probe is a handheld tool that is connected to the system console through a connector (not shown).

The system console includes a computer or controller 311 that governs operation of the system. Details of the console may be as discussed above and shown in FIG. 2. For example, an emitter 314 is analogous to signal emitter 231, and a detector 317 is analogous to signal detector 233.

The computer is connected to (or incorporates) emitter 314, detector 317, and a marking source 322. In an implementation, marking is by ink; in other implementations, however, other types of marking and their associated mechanisms may be used instead, or in combination with each other.

Within the computer, there is an ink controller 325 that governs operation of the inking mechanism. The ink controller functionality may be incorporated in the computer controller functionality of the system. However, in other implementations, the ink controller may be separate from the computer, such as implemented using a separate integrated circuit or chip.

The system probe includes a sensor 329 and an inker 333. The sensor of the probe is connected to the emitter and detector of the system console and the inker is connected to the ink source. Because the sensor and inker are part of the same probe, a location that the inker marks will generally be in proximity to the sensor. In a specific implementation, the inker is positioned within about 10 millimeters of one the sensors (e.g., an edge of an emitter or detector opening). In other implementation, the inker is position within about X millimeters of a sensor, where X is any value such as 18, 17, 16, 15, 12, 9, 8, 7, 6, 5.8, 5.5, 5, 4, 3, 2, or 1.

To measure oxygen saturation, the sensor of the probe is placed on a target tissue 335 where a measurement is desired. Light is generated at the emitter and transmitted through a connection 337 to the sensor. This light is scattered into the tissue and some light is reflected back to the sensor, which is transmitted via a connection 341 to the detector. Based on the transmitted and received light, the computer (or controller) calculates the oxygen saturation of the tissue. A value can appear on a display (not shown) of the console.

After the oxygen saturation measurement is successfully made, the ink controller directs the inker (via the ink source) to mark the target tissue. The specific marking mechanism in this figure is an inking mechanism. But, there are many other techniques and mechanisms for marking tissue, and any of these techniques may be used instead of, or in conjunction with, ink.

For example, some other marking techniques include using tattooing, dyes, pigments, stickers, chemicals, toner, acids, bases, ultraviolet, laser, infrared, radiation, etching, thermal, liquid, heat, burning, branding, and many others. One or more tissue marking techniques can be used in combination with each other.

The inking mechanism shown in this figure includes the ink controller, ink source, and inker. The ink controller determines when and how to mark the tissue. A controller can be implemented using an electronic circuit (e.g., one or more integrated circuits) with the logic to control the inking function. This logic can include combinatorial logic (e.g., NAND gates and NOR gates) or sequential logic (e.g., flip flops, registers, and state machines), or both. The controller can also be implemented using software or firmware, which directs operations of a programmed machine (e.g., a computer).

The ink source is a reservoir of ink or other material used for marking the tissue. The inker is, for example, a tip, nozzle, or head of the inking mechanism which emits the ink that marks the tissue.

The inker head can have any size, shape, or form. A larger-sized inker will generally make a larger mark, while a smaller-sized inker will make a smaller mark. If a smaller-sized inker is used, multiple marks may be used in order to increase its size or prominence. Some additional examples of forms of an inker include a sponge, a pipette, or a stamp. Some examples of shapes of an inker include rectangle, circle, dot, square, line drawing, or character (e.g., letter or symbol). An inker may include any combination of sizes, forms, and shapes. For example, the inker may have multiple nozzles.

The inker can mark the tissue in a number of ways. Some specific techniques are to drop a droplet of ink on the tissue (see FIG. 4), spray ink on the tissue (see FIG. 5), and stamp the tissue (see FIG. 6). Any of these or other marking techniques may be used. The specific mark made on the tissue is usually related to the shape or form of the inker head.

For example, when the inker is a circle stamp, then the resulting mark will be a circle on the tissue. If the inker is a nozzle, then the inker can place multiple droplets in the form of a particular shape or character. Additionally, the inker may mark using multiple droplets of ink on the tissue, such as two drops, three drops, four drops, or more.

In an implementation, the system provides a marking mechanism having a single color, such as a single ink color. In an implementation, the ink source is a reservoir that holds a single ink color (such as black). As directed by the controller, ink is delivered from the ink source to the inker via a connection 343, which may be a tube. For example, ink may be forced out of the ink source to the inker head using a pressure pulse (such as caused by a piezoelectric material or pump).

In an implementation, there is only one cable interface which connects (i) the emitter and sensor, (ii) the detector and sensor, and (iii) the ink source and inker. In an alternative implementation, there is more than one connection interface. For example, there is a first cable interface that has (i) and (ii) and a second cable interface that has (iii). As another example, there is a first cable interface that has (i), a second cable interface that has (ii), and a third cable interface that has (iii).

When the reservoir becomes low or empty, the user can refill the reservoir with additional ink or other material. The system may give a visual or audible indication on the screen of the console when the reservoir is low or the ink source needs to be replaced. It is desirable that the ink is nontoxic, so it does not cause harm to the tissue or patient.

In a specific implementation, the ink source is a replaceable ink cartridge, which can be disposed of after use. When an ink cartridge is empty, it may be removed from a receptacle of the console and replaced with a like cartridge that is full. By using replaceable ink cartridges, users may replace ink with less likelihood of spilling ink during the replacement process, especially compared to using an eye dropper to transfer ink from an ink bottle. Further, each cartridge may be sealed and have an expiration date, which ensures their effectiveness.

In another implementation, at the option of the user, used ink cartridges may be refilled and then used again. Or the cartridges can be remanufactured and then used again. This will help reduce the amount of waste going to landfills.

In another implementation, the system provides a marking mechanism having multiple colors, such as two or more ink colors. There can be any number of colors, two, three, four, five, six, seven, eight, or more colors. Some examples of colors include red, green, blue, cyan, orange, magenta, yellow, and black. There can be various hues, tints, shades, or intensities of the same color. Ink for multiple colors can be refilled or replaced similarly as discussed above.

With multiple ink colors, there are multiple ink reservoirs, one reservoir for each ink color. Multiple colors of ink may also be supplied using multiple replaceable ink cartridges or a single replaceable cartridge including multiple colors. A disadvantage of using a single replaceable cartridge having multiple colors is that when one color is used up, the entire cartridge will need to be replaced even though ink remains for one or more of the other colors.

For an implementation of the invention where there are multiple ink colors, each ink color is derived an ink source that is connected via a tube to an inker head. In one implementation, for each ink color, there is one tube connecting an ink source to an inker head. So, for three colors, there will be three tubes and three inker heads. However, in an alternate implementation, there is a single inker head that receives ink from tubes connected to the different color ink sources.

Figure 4:
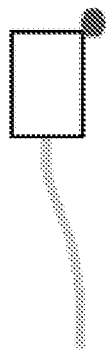
FIG. 4 shows marking a tissue using a drop.
Figure 5:
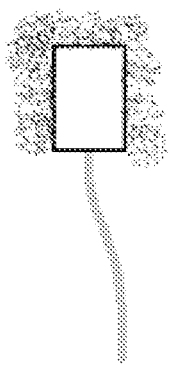
FIG. 5 shows marking a tissue using a spray.
Figure 6:
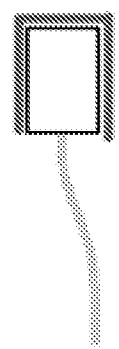
FIG. 6 shows marking a tissue using a stamp.

FIGS. 4, 5, and 6 show three different ways of marking a tissue. For example, the marking may be at a tissue surface, above a location where a measurement has been made. FIG. 4 shows an inker that drops ink onto the surface of a tissue. FIG. 5 shows an inker spraying ink on the tissue. FIG. 6 shows an inker stamping the tissue. Any of these techniques of marking may be used individually, or they may be used in any combination with each other, or in combination with other marking techniques.

For example, one marking variation involves using multiple drops on the surface of a target tissue. Further, other marking techniques not specifically discussed in this application may also be used in conjunction with the invention.

Figure 7:
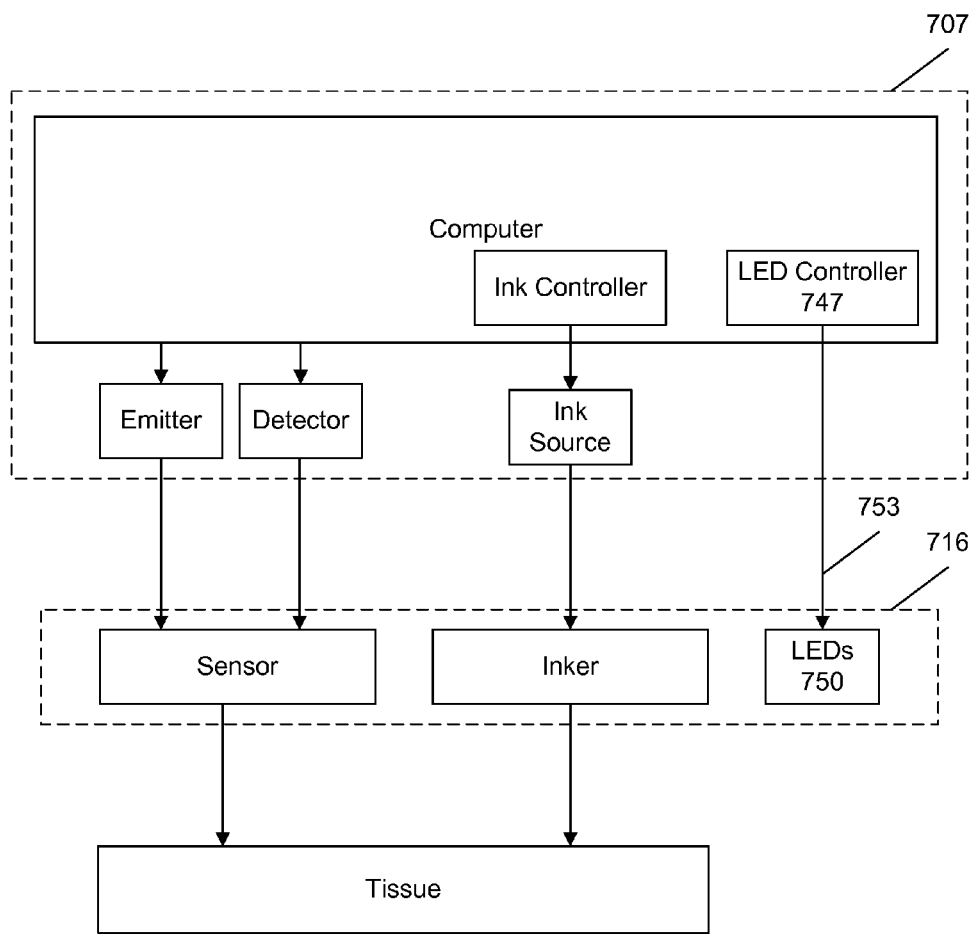
FIG. 7 shows a block diagram of an oximeter system incorporating a marking feature and LEDs.

FIG. 7 shows a block diagram of another implementation of a system of the invention. This implementation is similar to the implementation in FIG. 3. Compared to the system in FIG. 3, there are two additional components: an LED controller 747 in the console 707 and LEDs 750, or other visible light sources, on the probe 716.

As discussed above, emitter 314 may be implemented using light sources such as laser diodes and LEDs. In contrast to the light sources used for emitter 314, LEDs 750 and light sources are used as indicators for the user and not used in measuring oxygen saturation.

Light from emitter 314 is transmitted to sensor into the tissue to be measured. Consequently, the sensor or emitter is usually on a tissue-facing surface of the probe. When the probe is used, the tissue-facing surface and the sensor are generally hidden or not visible by the user because this surface faces and touches (or is close to) the tissue surface. In contrast, LEDs 750 are positioned to be visible to the user, even when the probe is used. Any indicator lights (e.g., LEDs 750) are positioned on the probe on a surface other than or different from the tissue-facing surface of the probe. Indicator lights will be on a non-tissue-facing surface. For example, LEDs 750 are positioned on a side, top, or near a handle of the probe. See FIG. 14 for an example of positioning of some LEDs.

Further, in an implementation, emitter 314 provides narrowband light at a specific wavelength. In comparison, LEDs 750 provide a wider band of light (e.g., wide spectrum green, yellow, or red light). Also, the power output of emitter 314 will generally be higher at the specific wavelength than provided by a wider band light source such as LED 750. For example, in an implementation, the power output of emitter 314 is about 3 milliwatts at the particular wavelength (e.g., 690 nanometers or 830 nanometers). Emitter 314 typically provides greater power output, especially at the desired wavelength, than one LED 750.

For visible light, violet light has a wavelength band from 380 nanometers to 450 nanometers. Blue light has a wavelength band from 450 nanometers to 495 nanometers. Green light has a wavelength band from 495 nanometers to 570 nanometers. Yellow light has a wavelength band from 570 nanometers to 590 nanometers. Orange light has a wavelength band from 590 nanometers to 620 nanometers. Red light has a wavelength band from 620 nanometers to 750 nanometers.

Infrared-A light has a wavelength band from about 700 nanometers to 1400 nanometers. Infrared-B light has a wavelength band from about 1400 nanometers to 3000 nanometers. Infrared-C light has a wavelength band from about 3000 nanometers to 1 millimeter. Light having a wavelength of 830 nanometers is not visible.

In an implementation, emitter 314 is located within the console, while LEDs 750 are located at the probe. In another implementation, emitter 314 is located on a tissue-facing surface of the probe, while LEDs 750 are located on a non-tissue-facing surface of the probe.

In an implementation, an oxygen saturation measurement is made and then LEDs 750 are illuminated (or turned off— when using negative Boolean logic) to give an indication of the measured oxygen saturation. Therefore, emitter 314 is turned on before LEDs 750 will give an indication of the measured oxygen saturation by either turning on or turning off LEDs 750.

In an implementation (i.e., positive Boolean logic), emitter 314 and LEDs 750 will not be turned on at the same time. In an implementation (i.e., negative Boolean logic), emitter 314 will not be on at the same time LEDs 750 are off.

In contrast to emitter 314, LEDs 750 can be activated in many different ways. For example, in an implementation, a system uses one threshold oxygen saturation value in determining whether to activate one LED. If the obtained oxygen saturation measurement falls below the threshold value, then the LED is not turned on. If the obtained oxygen saturation measurement is above the threshold value, then the LED is turned on. Thus, activation of LED 750 depends solely upon the oxygen saturation measurement value. LEDs 750 are not involved in obtaining the measurement.

In another implementation, there are two LEDs. If an oxygen saturation measurement falls below a threshold value, a first LED is activated. The first LED may, for example, emit yellow light. If an oxygen saturation measurement falls above a threshold value, a second LED is activated. The second LED may emit green light.

Thus, LEDs 750 can have multiple characteristics. For example, they can emit multiple colors. In another implementation, the LEDs can use a variety of flashing mechanisms. In various implementations, LEDs 750 provide a greater number of colors than emitter 314. LEDs 750 provide only visible light while emitter 314 provides not visible light. LEDs 750 provide only visible light while emitter 314 provides not visible light and visible light. LEDs 750 are larger in size then emitter 314. LEDs 750 are smaller in size then emitter 314. There are greater numbers of LEDs 750 than emitters 314. There are greater numbers of emitters 314 than LEDs 750.

Although LEDs or light emitting diodes are specifically shown and discussed, other implementations of the invention may use other lighting or visualization techniques and means. Some examples include light bulbs, organic LEDs (OLEDs), plasma, LCD, fluorescent tube, and electroluminescent material. Some visualization techniques do not use active light emitters, but rely on ambient lighting; some examples include electronic paper and an LCD without backlighting.

The LED controller and LEDs, or other visible light sources, are components of a visual indication mechanism. The LED controller governs operation of this mechanism. As discussed above, such a controller may be implemented using electronic circuitry. The LED controller functionality may be incorporated in the computer controller functionality of the system as shown in FIG. 7. However, in other implementations, the LED controller may be separate from the computer, such as implemented using a separate integrated circuit or chip.

The LED controller determines when and how to activate the visible light source. The LED controller is connected to and activates the visible light source of the system probe via an electrical connection 753, typically a wire or cable.

The LEDs, or other visible light sources, on the probe are light-emitting diodes or other light source that emit visible light once activated by the LED controller. In a system, there can be any number of LEDs, one, two, three, four, or more than four. In the case where there are multiple LEDs, in addition to a power and ground connection to each LED, there may be a single wire from the controller to connect to each LED. The wires can be incorporated in a cable carrying all the LED wiring; additionally, this cable may also include the wiring to the sensor and inker.

The LED controller will activate and light the visible light source based on any number of preprogrammed factors or user-selected factors. For example, the visible light sources can be used to flash, thus indicating a system error condition, battery low condition, low ink source condition, connector error condition, or other conditions.

In a specific implementation, the lighting of the LEDs is based on oxygen saturation measurements determined by the system console. In this implementation, the LEDs, or other visible light sources, are located on the probe of the system in order to make the visual indication of tissue oxygen saturation convenient for the user of the system to see.

In an alternative implementation, the visual indication (the LEDs or other visible light sources) is placed on or near the system console. However, for such an implementation, it may be more difficult or inconvenient for the user to see the visual indication because the console may be located some distance away from the user and patient.

Having the LEDs on the probe, as illustrated in this figure, improves the efficiency of verifying the oxygen saturation calculated by the system console in that the system user can see the visual indication while applying the sensor of the system probe to the patient's tissue. Placement of the LEDs, or other visible light sources, on the probe also allows the system user to verify that the inker marks the tissue in a manner that corresponds to the particular activation of the LEDs.

There may be one or multiple (two or more) visible light sources and each visible light source may be of any size. Generally, the larger the visible light source, the easier it will be for the system user to see. However, if a smaller-sized visible light source is used, multiple visible light sources may be placed in a closely-spaced arrangement so that, when the arrangement is activated, the combination of smaller-sized visible light sources may increase their visibility.

Additionally, the visual indication of an LED, or other visible light source, may take the form of any shape or character (i.e., a letter or symbol) via placement of a cover or mask over the LEDs. Some examples of shapes of a light cover include a rectangle, circle, triangle, or square. The LEDs may also take any combination of sizes and forms. For example, an LED may in the form of a large square, a small rectangle, or four small circles in close proximity to each other to increase their visibility. A segmented or custom LED or LCD display panel may also be used.

One or more LEDs may be placed anywhere on the probe. For example, one or more visible light sources can be located on the end of the probe that is closest to the sensor and inker. Conversely, one or more visible light sources can be located closer to the handle of the probe, or somewhere in between.

If there are multiple LEDs, they may be arranged in any formation. Some examples of various formations include a cluster, a row, a column, or other linear formation. Multiple LEDs can also be arranged to form a certain shape, such as a square, rectangle, circle, or triangle.

When activated by the LED controller, the visible light sources on the system probe can emit light via any signaling mechanism. For example, the LEDs will flash when activated (e.g., rapid flashing, short flashes with a pauses between flashes, three flashes and a pausing before repeating this pattern, and flashing according to any pattern or frequency). Conversely, they can stay lit for an extended period of time, such as until marking by the marking mechanism (detailed in the description of FIG. 3) is complete. Any combination of signaling mechanisms may be incorporated into this system.

In a specific implementation, the system of the invention provides a visual indication mechanism where there is only one LED on the system probe. One visible light source may emit one color or multiple colors, such as two, three, four, or more.

In an implementation of one LED on the system probe, an LED may emit a single color, such as blue light. When directed by the computer, the LED controller may activate the LED on the probe, causing the LED to emit blue light.

In another implementation of one visible light source on the system probe, the visible light source may be capable of emitting multiple (two or more) colors and may emit each color at a different time, depending upon the direction provided by the LED controller. There may be any number of colors. Some examples of colors include blue, green, red, orange, and yellow. There may be various hues, tints, shades or intensities of the same color.

In a specific implementation, the system of the invention provides a visual indication mechanism with multiple visible light sources on the system probe. There may be any number of visible light sources: two, three, four, five, six, or more visible light sources. Multiple (two or more) visible light sources may be used to emit one color or multiple colors.

In an implementation of multiple LEDs on the system probe, a single LED color, such as green, may be used. If the LEDs are small in size, multiple LEDs may be used to increase their visibility. For example, the LED controller may activate four small LEDs arranged, for example, in a cluster on the probe, causing each of the LEDs to emit green light. An alternative implementation, for example, may involve three large LEDs that emit green light. In this example, the LED controller may determine the number of LEDs (one, two, or all three) to activate depending on information received by the system computer.

In another implementation of multiple LEDs on the system probe, each LED may correspond to a particular color. It may be desirable to have multiple (two or more) LEDs, then, when multiple colors are used. The LED controller may activate one LED (i.e., an LED that emits one color, such as blue light) at one point in time and a different LED (i.e., a different LED that emits a different color, such as green light) at a different point in time, or multiple LEDs (i.e., an LED that emits blue light and a different LED that emits green light) at the same time. The LED controller may activate any LED at any time and may alternate between LEDs or continue to activate the same LED, depending upon direction from the system computer. A given LED may emit any color in any hue, tint, shade or intensity of that color.

Figure 8:
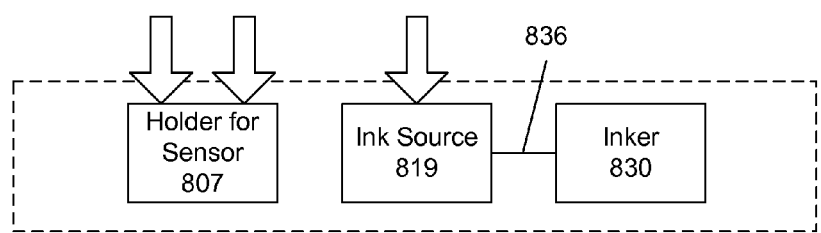
FIG. 8 shows a block diagram of a marking probe which has a holder for a sensor.

FIG. 8 shows a block diagram of a marking probe which has a holder for a sensor 807, a marking source 819, and a marking mechanism 830. The holder has a retaining mechanism (e.g., a retaining clip, clamp, or cavity) where a sensor unit of an oximeter (e.g., sensor 329) can be attached. The sensor unit may a small rectangular block with a cable. The probe is typically a handheld unit and includes a handle (see FIG. 14).

One implementation of the retaining mechanism involves a clamp, clip, or band. For example, the holder may incorporate a clamp that grasps the sensor. To remove the sensor from the probe, the clamp may be released. The sensor is removably connected to the probe, which means the user can attach the probe and remove it from the probe as desired. Since the sensor is removable, the sensor can be disposed after it is worn out or after use on a particular person. Then the probe can be used again with another sensor.

In an implementation, this marking probe is used in conjunction with a system unit or console, such as shown in one of the previous figures and described above. There is a cable that connects to the sensor in the holder (indicated by two arrows in the figure) and a cable that connects to the ink source (also indicated by an arrow). These components of the probe are connected via a cable to the console as discussed above.

For this implementation, the system console calculates an oxygen saturation measurement for a tissue and displays the measurement value via the console display. In addition, the marking probe marks the tissue such that the tissue mark corresponds to the oxygen saturation measurement shown on the computer display.

In an implementation, the marking probe is a standalone marking probe, which means that it is can be used without necessarily attaching it to a system unit or console. This standalone marking probe incorporates the circuitry necessary to calculate oxygen saturation measurements and determine marking mechanism outputs. The sensor is connected to the circuitry within the probe (e.g., the probe includes the light emitter and light detector). In use, the user will receive an indication on the measured oxygen saturation via the marking mechanism and the display of the console is not needed.

For example, a user can identify an oxygen saturation measurement of a tissue by looking at a mark on the tissue. Specifically, an oxygen saturation measurement above 80 percent may yield a green tissue mark. Thus, by looking at the green tissue mark, the user knows the oxygen saturation of the tissue is in an acceptable range without having to look at a computer system display.

There are many different structures and mechanisms that can be used to allow the sensor to removably attach to the holder and probe. For example, in an implementation, the sensor casing has a built-in tab or other similar retaining feature that locks the sensor in place in the holder. One can press the tab and to release the sensor from the probe. Or a button may be pushed to release the sensor from the holder.

In another implementation of the retaining mechanism, a sensor unit is placed into a cavity of the probe and latched in place. The sensor unit can be removed from the probe by unlatching and pulling it out of the cavity.

Also, this figure shows the marking source located within the probe; however, in another implementation, the marking source is external to the probe. Then, the ink source is connected to the inker of the probe via a cable (not shown). This implementation is more similar to probe 308 of FIG. 3.

Further, the marking source may be removably attached to the probe, similar to how the sensor is removably attached. Any structure or retaining mechanism that allows the marking source to be removably attached to the probe can be used. Then when the ink source runs out of ink, the user can remove an ink cartridge and replace it.

In another implementation, the marking source is not user replaceable. For this implementation, it is intended that once the ink has run out, the user will dispose of the probe and use a new probe. Therefore, the probe itself is disposable, and the sensor for the probe is disposable too. In this case, for each use of one probe, a user may use and dispose of a number of sensor units. For example, the individual sensor units are used one per patient. And the probe is used until the ink runs out.

Marking material is delivered from marking source 819 to marking mechanism 830 via a connection 836. In the case of ink, connection 836 is typically a tube or capillary to deliver ink. For example, marking material may be forced out of the marking source to the marking mechanism using a pressure pulse (such as caused by a piezoelectric material or pump).

In another implementation, there are multiple (two, three, four, or more) ink reservoirs for multiple ink colors, such as blue, purple, and orange. In this implementation, if the blue ink runs out, the user may dispose and replace the blue ink reservoir. Conversely, if the ink reservoirs are contained in a single unit, the user may have to dispose of the entire ink reservoir unit even if the purple and orange ink reservoirs have not run out.

In an implementation, the marking mechanism may be disposable after each use. For example, the marking mechanism can be integrated with the sensor unit. In a specific implementation, the marking mechanism is an inking mechanism. An implementation involves disposing of the inking mechanism after each use within one procedure; another implementation involves disposing of the marking mechanism after one entire procedure is completed.

Figure 9:
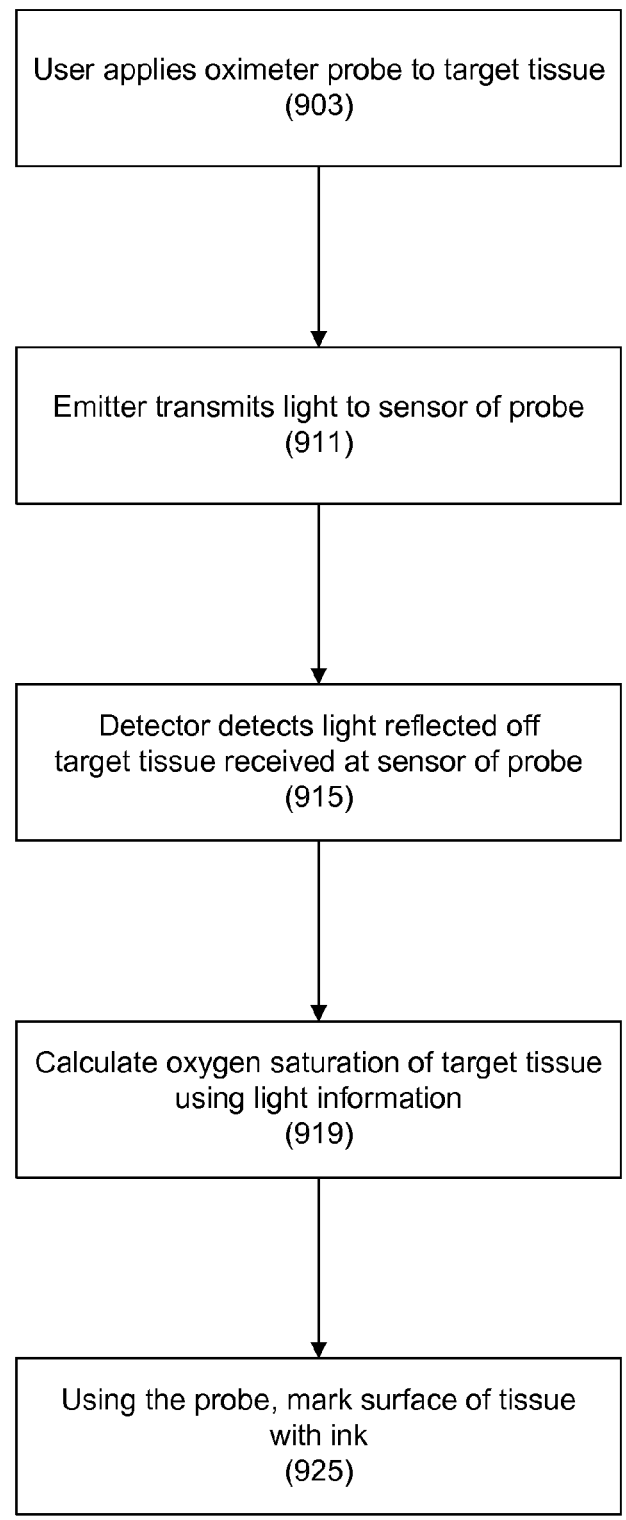
FIG. 9 shows a flow diagram for operating a tissue oximeter having a marking feature.

FIG. 9 is a flow diagram of a marking feature of the invention which can be incorporated into a system designed to measure oxygen saturation of tissues. In this specific implementation, the marking feature is an inking feature that enables marking of a tissue surface with one ink color.

First, in step 903, a user applies a tissue oximeter probe to a target tissue. The user may be a doctor or any other medical professional. Typically, the user, who wishes to determine the oxygen saturation of a particular tissue, may apply a sensor of the tissue oximeter probe to the surface of the skin in order to obtain this measurement.

When the sensor touches or is in contact with the target tissue, in step 911, a computer (or controller) directs an emitter (connected to the sensor and computer) to transmit light to the sensor of the probe, and into the target tissue. After the light is transmitted into the tissue, some of the light is reflected off of the tissue.

In step 915, a detector (connected to the sensor and computer) detects the light reflected off of the target tissue; this information is received at the sensor of the probe. The detector then sends this light information to the computer.

The computer, in step 919, calculates the oxygen saturation of the target tissue using this light information. Then, the computer directs an ink controller to activate an ink source which connects to an inker.

In step 925, the inker marks the tissue surface with ink. This implementation of this inking feature involves the application of any color to the surface of the target tissue. The inking feature may be used represent a tissue location. A single ink color may also be used, for example, to identify a location of the tissue where the oxygen saturation is at critically low levels, or at normal levels. A single ink color may essentially be used for any identification purposes.

For example, a mark is made when the oxygen saturation measurement is low, and no mark is made when the oxygen saturation measurement is satisfactory. Then the doctor will have a map of where the oxygen saturation readings are not at acceptable levels.

A variation of this implementation involves the use of a single ink color, such as black, and a marker capable of marking a tissue in two, three, four, or more ways, such as with multiple shapes or droplets. For instance, black squares can indicate low oxygen saturation levels of a tissue, while black triangles represent elevated oxygen saturation levels of the tissue. One drop represents one thing, while two drops represent another.

Figure 10:
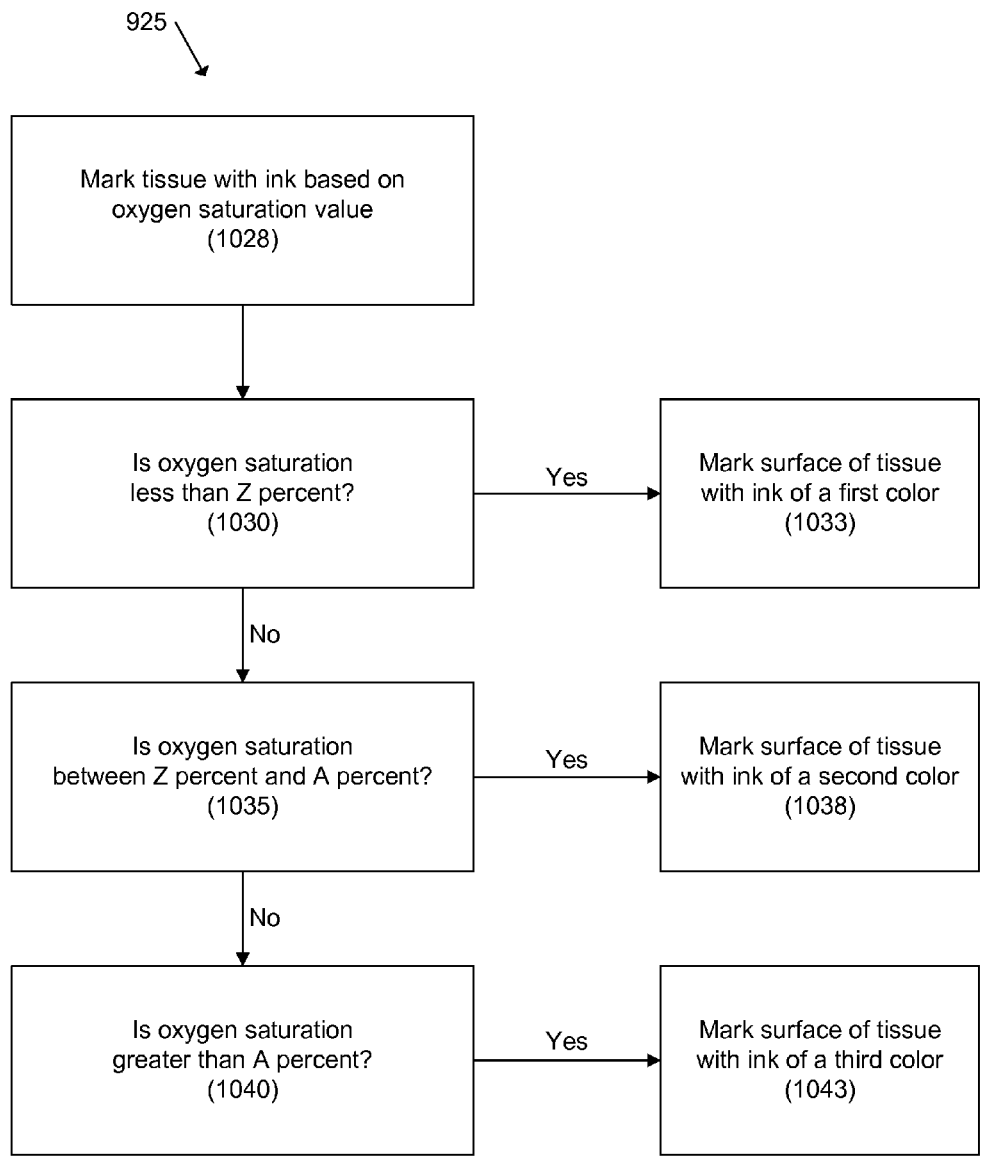
FIG. 10 shows a flow diagram for using multiple marking colors to indicate oxygen saturation levels.

FIG. 10 shows a flow diagram of an inking feature which can be incorporated into a system designed to measure oxygen saturation of tissues. This inking feature allows for the use of multiple ink colors in marking the surface of a target tissue, where each color corresponds to a particular oxygen saturation range.

The oxygen saturation range may be selected by the user or predetermined by the factory. Depending on the oxygen saturation level of the target tissue, a particular ink color will be used to mark the surface of the target tissue.

The ranges may be specified using threshold values, each of which may be factory set or user specified. For example, a user may enter threshold values for when a mark (perhaps of a certain color) should be made, such as through a touch screen of the console. Although this application gives some specific examples of values for the thresholds (e.g., 30 percent and 40 percent) the values may be Z percent and A percent, which are any number, where A is greater than Z.

In a specific implementation, the initial process of taking an oxygen saturation measurement and marking the tissue surface is exactly the same as that presented in FIG. 9 (steps 903 through 925). However, in this implementation, step 1028 shows that the inker marks the tissue surface with colored ink based on the oxygen saturation value determined by the computer.

As an example of this implementation, in step 1030, if the oxygen saturation is less than Z percent, then in step 1033, an inker marks the surface of a tissue in an ink of a first color. Specifically, for example, if the oxygen saturation is less than 30 percent, then an inker marks a tissue surface with red ink.

If the oxygen saturation is not less than Z percent, then the computer considers step 1035. In step 1035, if the oxygen saturation is between Z percent and A percent, then, in step 1038, an inker marks a tissue surface in an ink of a second color, where the second color is different from the first color. For example, if the oxygen saturation is between 30 percent and 40 percent, then an inker marks a tissue surface in yellow ink.

If the oxygen saturation is not less than A percent and, thus, does not fall under steps 1030 or 1035, then the computer considers step 1040.

In step 1040, if the oxygen saturation is greater than A percent, then, in step 1043, an inker marks a tissue surface with an ink of a third color, where the third color is different from the first and second colors. For example, if the oxygen saturation is greater than 40 percent, then an inker marks a tissue surface in green ink.

In a specific implementation, any color can be used and the threshold values can be any number. Although in this implementation 30 percent and 40 percent are used as examples of threshold values, any percentage, range, or number may be used as a threshold value in another implementation.

One implementation may involve the use of one threshold value. Oxygen saturation levels falling at or below that value initiate the use of one color while oxygen saturation levels falling above that value initiate the use of another color.

The oxygen saturation ranges need not be equal. For instance, blue ink may be used when oxygen saturation levels fall at or below 20 percent and black ink may be used when oxygen saturation levels fall above 20 percent.

A variation of this implementation involves the use of two equal ranges where blue ink is used for oxygen saturation values at or below 50 percent and black ink is used for oxygen saturation values above 50 percent.

Yet another implementation may involve the use of four threshold values and five corresponding colors. Any number of threshold values and corresponding colors may be used. For example, there may be two threshold values and three corresponding colors, five threshold values and six corresponding colors, or more.

The use of multiple ink colors has diverse applications. For instance, various areas of one tissue may be easily identifiable through the use of multiple colors, with each color representing a corresponding oxygen saturation measurement of that particular tissue area. Similarly, multiple tissues of various areas can be identified with different colors depending upon their respective oxygen saturation measurements.

A variation of this implementation involves the use of multiple colors, in combination with multiple marking techniques. For instance, a blue square may represent low oxygen saturation levels of a tissue, while an orange circle represents elevated oxygen saturation levels of the tissue.

Figure 11:
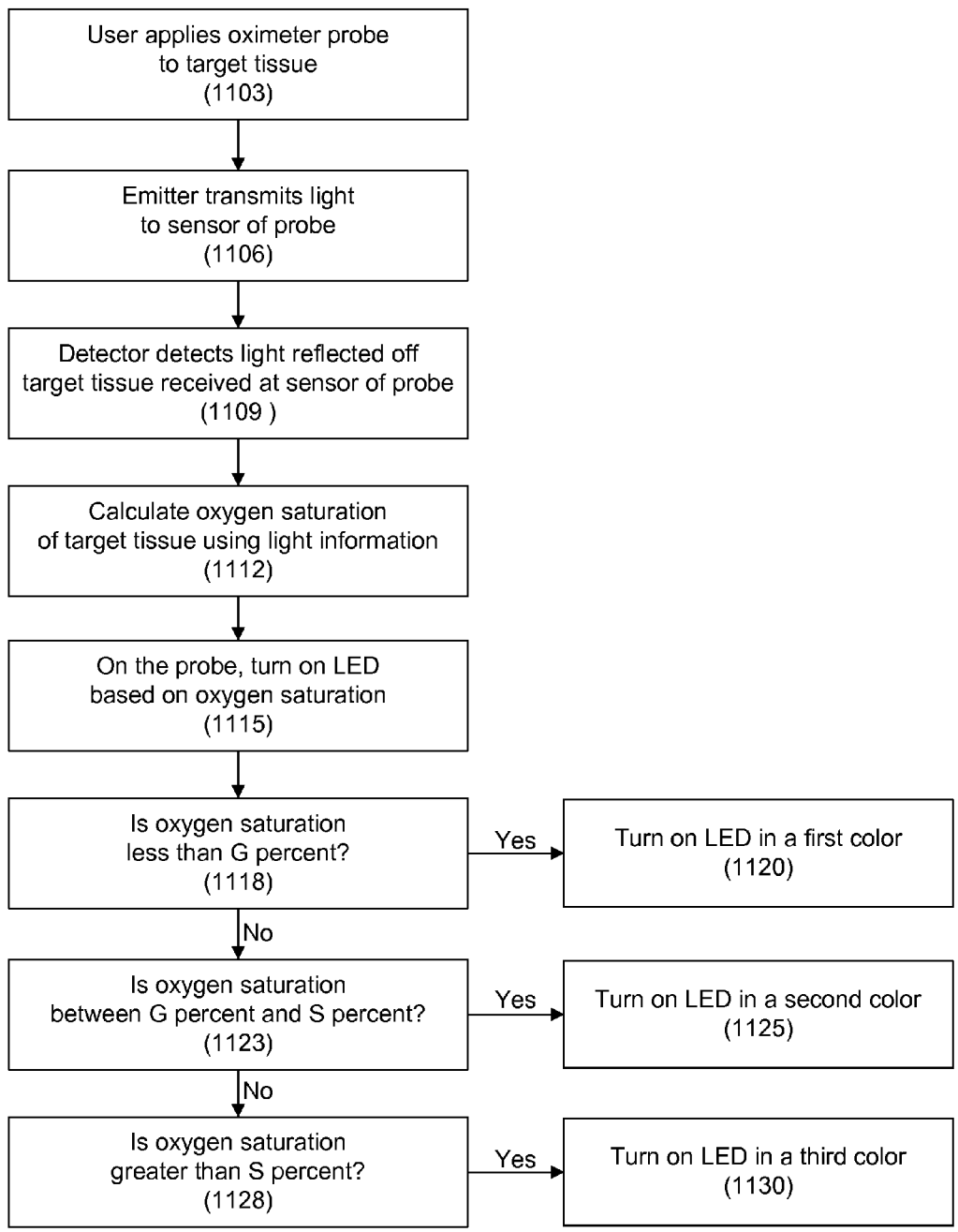
FIG. 11 shows a flow diagram for using multiple LED colors to indicate oxygen saturation levels.

FIG. 11 shows a flow diagram for the activation of LEDs, or other visible light sources, which may be incorporated into a probe of a system designed to measure oxygen saturation of tissues. This implementation allows for the use of multiple LEDs, with each LED color corresponding to a particular range or value of the target tissue's oxygen saturation. Depending on the oxygen saturation level of the target tissue, a particular LED color will be turned on.

Similar to FIG. 9, in step 1103, a user applies a tissue oximeter probe to a target tissue In steps 1106 and 1109, the computer receives the light information (via the emitter and detector) from the sensor touching the target tissue. Using the light information, in step 1112, the computer then determines the oxygen saturation of that tissue and activates an LED controller which, in step 1115, activates the LEDs (or other visible light sources) on the probe.

The ranges may be specified using threshold values, each of which may be factory set or user specified. For example, a user may enter threshold values when an LED be turned on, such as through a touch screen of the console. Although this application gives examples of specific values for the thresholds (e.g., 30 percent and 40 percent) the values may be G and S, which are any number, where S is greater than G.

In a specific implementation, in step 1118, if the oxygen saturation is less than G percent, then, in step 1120, an LED (or other visible light source) emits light of a first color. For example, if the oxygen saturation is less than 30 percent, then a red LED turns on. If the oxygen saturation is not less than G percent, then the computer considers step 1123.

In step 1123, if the oxygen saturation is between G percent and S percent, then, in step 1125, an LED (or other visible light source) emits light of a second color, where the second color is different from the first color. For example, if the oxygen saturation is between 30 percent and 40 percent, then a yellow LED turns on. If the oxygen saturation is not less than S percent and, thus, does not fall under steps 1118 or 1123, then the computer considers step 1128.

In step 1128, if the oxygen saturation is greater than S percent, then, in step 1130, an LED (or other visible light source) emits light of a third color, where the third color is different from the first and second colors. For example, if the oxygen saturation is greater than 40 percent, then a green LED turns on.

In this implementation, an LED can emit any color and the threshold values can be any number or range. As discussed above in the description for FIG. 10, the threshold percentages of 30 percent and 40 percent are used as examples; in other implementations, other threshold values may be used.

This implementation may involve the use of one LED, or other visible light source, corresponding to one color. In such an implementation, a single LED color, such as blue, may be used to identify a location of the tissue where the oxygen saturation is at critically low levels, or at normal levels. A single LED color may essentially be used for any identification purposes.

In a variation of an implementation with one LED, or other visible light source, on the system probe, a single LED color may also indicate multiple conclusions when used in combination with various signaling mechanisms. For instance, an LED that emits blue light via a rapid flashing mechanism may represent critically low oxygen saturation levels of a tissue while an LED that emits blue light for an extended period of time may represent critically elevated oxygen saturation levels of the tissue.

In another variation of an implementation of one LED on the system probe, the LED, or other visible light source, may be capable of emitting multiple colors at different times, depending upon the oxygen saturation of a tissue (calculated by the system console). For instance, when the oxygen saturation of a tissue is low, the LED may emit blue light; when the oxygen saturation of a tissue is high, the same LED may emit orange light.

This implementation may also involve the use of two LEDs, or other visible light sources, each corresponding to a different color. In such an implementation, as with the inking function described in FIG. 9, each LED color corresponds to a particular range of oxygen saturation. The ranges need not be equal and there may be multiple ranges and threshold values, thus leading to the use of multiple LED colors. Yet another implementation may involve the use of five LEDs with each LED corresponding to a different color. The use of multiple LED colors, similar to the use of multiple ink colors in FIG. 9, has diverse applications.

Figure 12:
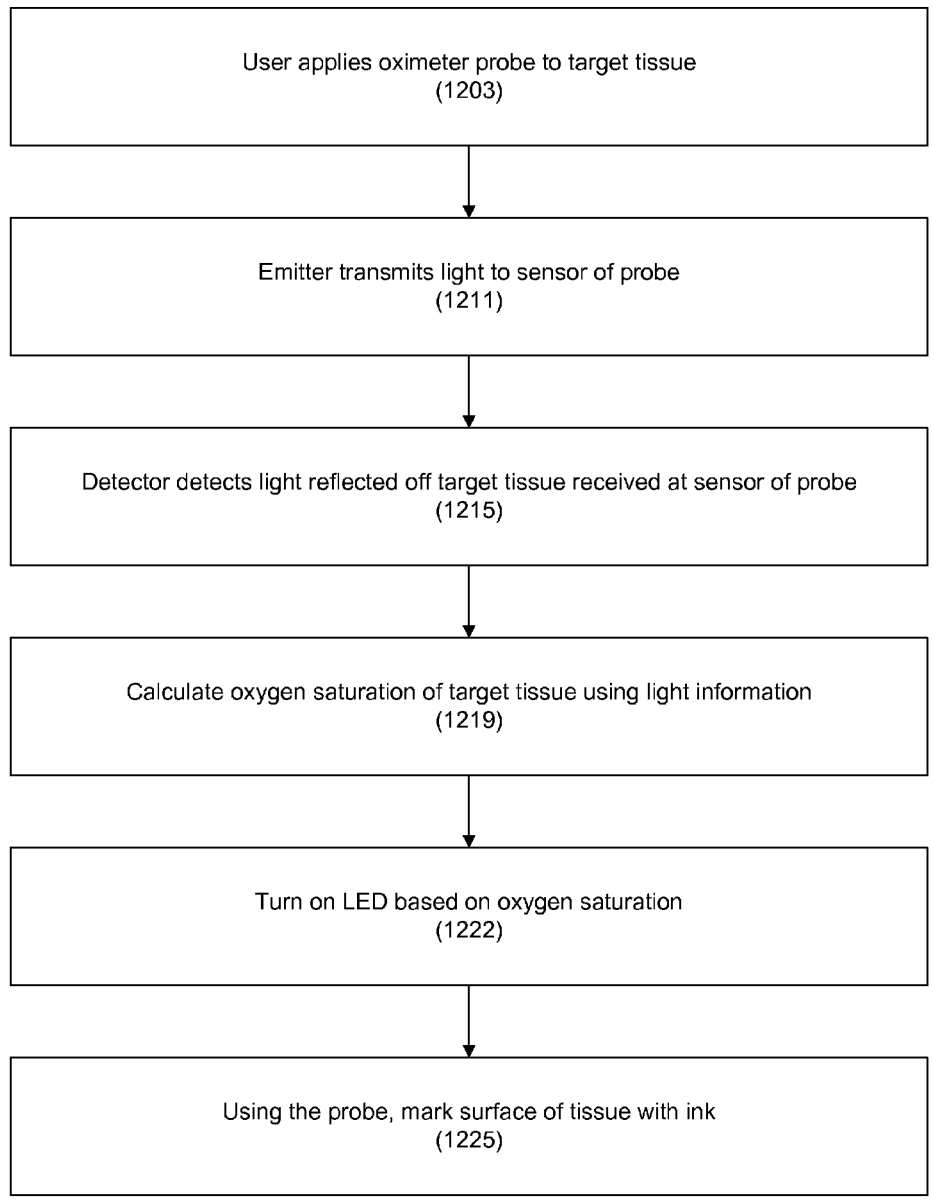
FIG. 12 shows a flow diagram for operating a tissue oximeter having a marking feature and LEDs.

FIG. 12 shows a flow diagram of the inking feature (or other marking feature) and LEDs (or other visible light sources), incorporated into a device that measures oxygen saturation of tissues. Depending on the oxygen saturation of a target tissue, a particular LED color may turn on and a corresponding ink color may be used to mark the surface of a target tissue.

Similar to FIGS. 9 and 11, in step 1203, a user applies a tissue oximeter probe to a target tissue. Then, in step 1211, an emitter transmits light to a sensor of a probe, and into the tissue. As some of the light is then reflected off of the tissue, in step 1215 a detector detects the reflected light; this light information is received at the sensor of the probe.

In step 1219, a computer, which connects to the emitter and detector, uses this light information to calculate the oxygen saturation of the target tissue.

Similar to FIG. 11, the computer then activates an LED controller which connects to LEDs, or other visible light sources, on the probe and, in step 1222, turns a visible light source on based on the oxygen saturation of the target tissue. One, two, three, or more LEDs may be used.

Additionally, similar to FIG. 10, the computer directs an ink controller to activate an ink source which connects to an inker. In step 1225, using the probe, the inker then marks the surface of the target tissue with ink based on the oxygen saturation of that tissue.

There may be various combinations of this implementation of the marking and visual indication mechanisms incorporated into an oximeter or similar medical device. For example, there may one LED (or other visible light source) and one ink (or other mark) color. Variations may include one LED and multiple ink colors, multiple LEDs and one ink color, or multiple LEDs and multiple ink colors.

Figure 13:
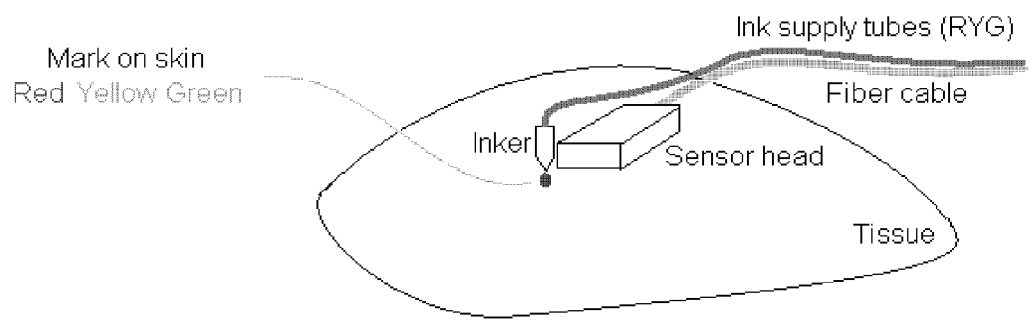
FIG. 13 shows a sensor head and inker of an oximeter device.

FIG. 13 shows an implementation of an inking mechanism connected to a sensor head of an oximeter. Once the oxygen saturation of a target tissue is determined, ink supply tubes provide red, yellow, or green ink to an inker, which then marks the surface of a target tissue to represent a location of a tissue and indicate an oxygen saturation measurement of the target tissue.

Figure 14:
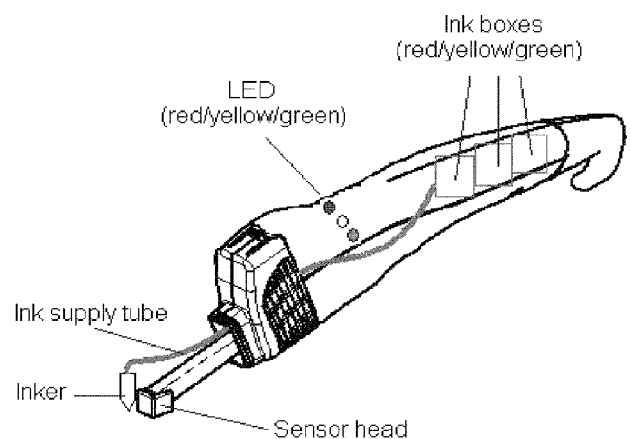
FIG. 14 shows a handheld probe having a handle, sensor head, LEDs, inker, and ink boxes.

FIG. 14 shows an implementation of an oximeter probe with inking mechanism. This probe includes visible light indictors sources on a probe of the oximeter. This probe may be a standalone probe or a probe that is to be connected to an oximeter console. This oximeter probe has an elongated handle allowing a user to more easily grasp the probe.

Depending upon an oxygen saturation measurement of a target tissue, a red, yellow, or green LED turns on. The color emitted by the LED corresponds with red, yellow, or green ink used to mark the surface of a target tissue. In other implementations, the ink colors of the mark do not necessarily match the colors of the indicators lights.

Further, within the handle are ink boxes or cartridges (e.g., red, yellow, and green) that are connected via a tube to an inker. In an implementation, there is only one ink for one ink color. In other implementations, the ink color of the mark is a mixture of the inks provided by the cartridges. For example, an orange color is obtained by combining red and yellow.

The ink boxed may be contained within the probe handle or attached to the probe handle. The probe may have an internal compartment that encloses the ink boxes. Further there may be translucent window to the ink boxes, so the user can visibly check the level of ink that is still available. In an implementation, the probe is disposable and is replaced with another probe when the ink boxes become empty. In an implementation, when the ink boxes become empty, the user can refill them.

The inker is held in proximity (e.g., within 10 millimeters) or adjacent to the sensor head. In some implementations, the inker may be held a fixed distance away form the sensor head; so when measurements and marks are made, one can look at the mark and find the location where a measure was made.

FIGS. 15-22 show various specific implementations of a sensor unit or sensor head. Each figure shows a particular opening pattern, and any of these may be used in conjunction with any of the implementations discussed in this patent. For example, a marking mechanism output may be positioned to be in proximity to a sensor unit or attached to the sensor unit. These figures show only some examples of opening patterns. There are other possible opening patterns and any of these other opening patterns, and their variations, may be used with the invention.

The sensor openings at the sensor head are typically connected via a fiber optic cable to the emitters and detectors of the console. The emitters are connected to a source sensor opening, and the detectors are connected to a detector sensor opening. However, in an implementation, the emitter and detectors are positioned at the sensor head and a fiber optic cable is not needed.

Figure 15:
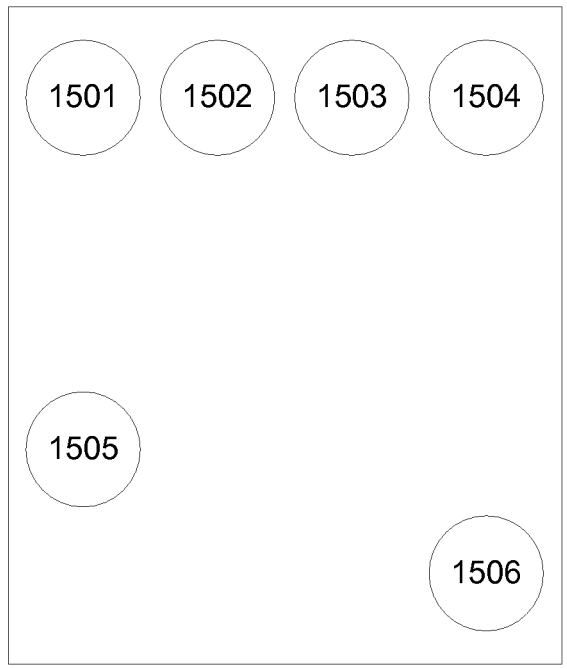
FIG. 15 shows a sensor opening pattern where one sensor opening is aligned asymmetrically with respect to the other sensor openings.

FIG. 15 shows a specific implementation of a sensor unit. Such a sensor unit may be incorporated in the various probe implementations (e.g., sensor 329 or sensor for holder 807) discussed above in this application.

This sensor has six openings 1501-1506. Openings 1501-1504 are arranged in a line closer to a first edge of the sensor, while openings 1505 and 1506 are arranged closer to a second edge, which is opposite the first edge. In fact, opening 1506 is closer than opening 1505 to the second edge. These openings are for sources and detectors, and there can be any number of sources, any number of detectors, and they can be in any combination. In an implementation of a sensor head, the first edge is distal to the second edge, which is closer to a cable attached to the probe or hand holding the probe.

In one implementation, openings 1501-1504 are detectors while openings 1505 and 1506 are sources. However, in other implementations, there can be one or more detectors, two or more detectors, one or more sources, or two or more sources. For example, there may be three detectors and three sources or one detector and five sources.

In FIG. 15, the openings are positioned asymmetrically such that a line drawn through openings 1501-1504 is not parallel to a line drawn through openings 1505 and 1506. However, a line drawn through openings 1501 and 1505 is parallel to a line through openings 1504 and 1506. Additionally, the distance between openings 1501 and 1504 is shorter than the distance between openings 1505 and 1506.

Thus, the distance between openings 1501 and 1505 does not equal the distance between openings 1501 and 1506; the distance between openings 1502 and 1505 does not equal the distance between openings 1503 and 1505; and the distance between openings 1503 and 1505 does not equal the distance between openings 1504 and 1506.

In this implementation, the sensor unit has a rectangular shape, but the sensor unit may have any shape such a trapezoid, triangle, dodecagon, octagon, hexagon, square, circle, or ellipse. A sensor of any shape or form can incorporate the sensor openings in the pattern shown and described.

In a specific implementation, a distance between openings 1501 and 1504 is five millimeters. A distance between each of the openings 1501, 1502, 1503, and 1504 is 5/3 millimeters. A distance between 1501 and 1505 is five millimeters. A diameter of an opening is one millimeter.

Figure 16:
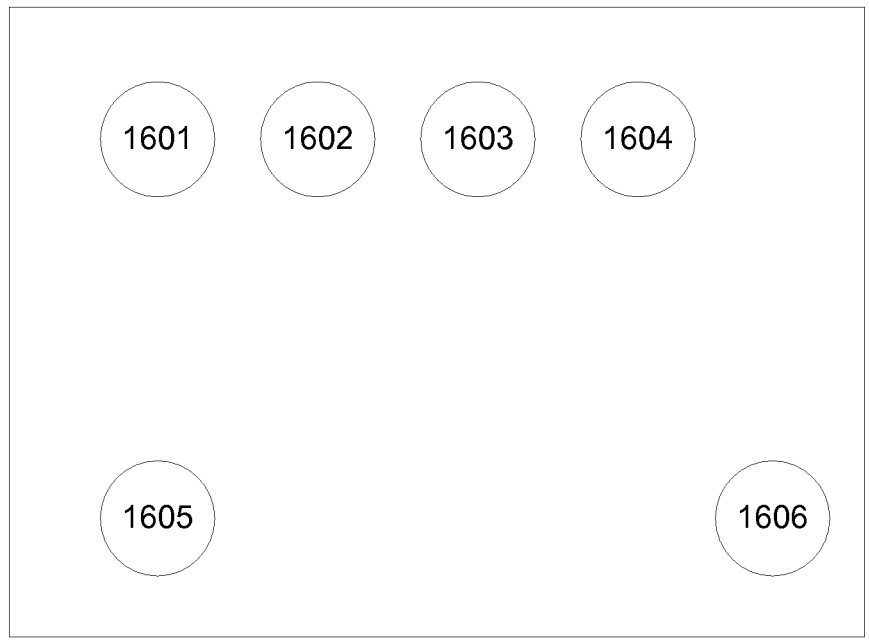
FIG. 16 shows another sensor opening pattern where one sensor opening is aligned asymmetrically with respect to the other sensor openings.

FIG. 16 shows a variation of the implementation of the sensor unit shown in FIG. 15. The sensor unit in this specific implementation is also arranged to include six openings 1601-1606. Similar to FIG. 15, openings 1601-1604 are arranged in a line closer to a first edge of the sensor, while openings 1605 and 1606 are arranged closer to a second edge, which is opposite the first edge. In one implementation, openings 1601-1604 are detectors while openings 1605 and 1606 are sources.

In this figure, the openings are positioned so that a line drawn through openings 1601-1604 is parallel to a line through openings 1605 and 1606. However, a line drawn through openings 1601 and 1605 is not parallel to a line through openings 1604 and 1606.

Additionally, similar to FIG. 15, the distance between openings 1601 and 1604 is shorter than the distance between openings 1605 and 1606. Thus, the distance between openings 1601 and 1605 does not equal the distance between openings 1601 and 1606; the distance between openings 1602 and 1605 does not equal the distance between openings 1603 and 1605; and the distance between openings 1603 and 1605 does not equal the distance between openings 1604 and 1606.

In this implementation, the sensor unit itself is of a greater area relative to the area of the sensor unit shown in FIG. 15. In another implementation, the sensor unit may be of a smaller area relative to the area shown in FIG. 15. In yet another implementation, the sensor unit may be of a greater area relative to that shown in FIG. 16.

Further, in a specific implementation, the openings are the same size as each other (e.g., each opening has the same diameter or each opening has the same area). A specific implementation uses one-millimeter circular openings. However, in another implementation, the diameter of one opening may be different from other openings, or there may be some openings with different diameters than other openings. There can be any combination of differently sized openings on one sensor unit. For example, there are two openings with a C size and other openings have a D size, where C and D are different and D is greater than C. Also, openings are not necessarily circular. So, C and D may represent area values.

Figure 17:
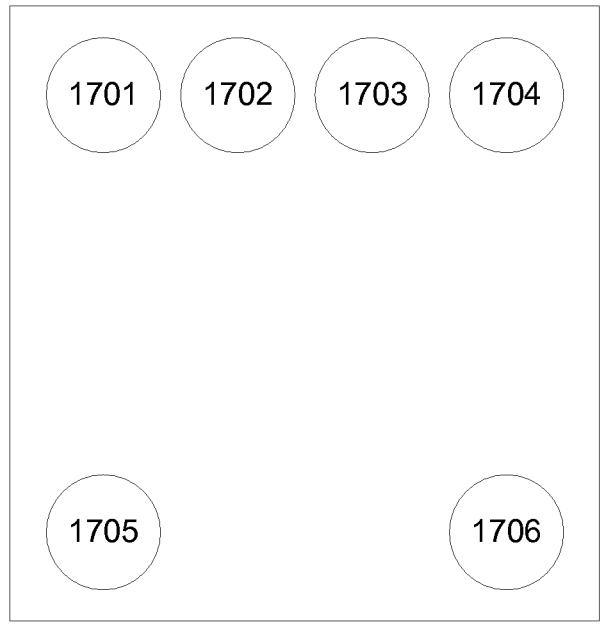
FIG. 17 shows a sensor opening pattern where the openings are arranged symmetrically about a vertical axis.

FIG. 17 shows another variation of the implementation of the sensor unit shown in FIG. 15. The sensor unit in this specific implementation is also arranged to include six openings 1701-1706. Similar to FIGS. 15 and 16, openings 1701-1704 are arranged in a line closer to a first edge of the sensor, while openings 1705 and 1706 are arranged closer to a second edge, which is opposite to the first edge. In one implementation, openings 1701-1704 are detectors while openings 1705 and 1706 are sources.

In this figure, the openings are positioned so that a line drawn through openings 1701-1704 is parallel to a line through openings 1705 and 1706. In fact, these two lines are equal in length. Furthermore, a line drawn through openings 1701 and 1705 is parallel (and equal in length) to a line through openings 1704 and 1706.

Thus, in this specific implementation, the distance between openings 1701 and 1706 is equal to the distance between openings 1704 and 1705. This specific arrangement includes further equalities: the distance between openings 1702 and 1705 equals that between openings 1703 and 1706 and the distance between openings 1703 and 1705 equals that between openings 1702 and 1706.

In an implementation, the distances between openings 1701-1704, 1704-1706, 1706-1705, and 1705-1701 are all equal; thus, in this implementation openings 1701, 1704, 1706, and 1705 form the vertices of a square. In other implementations, however, four openings may form the vertices of any quadrilateral, such as a rectangle, a rhombus, a trapezoid, or a parallelogram.

Aside from the equalities mentioned, the distances between each of the openings 1701-1704 and each of the openings 1705-1706 are not equal. For instance, the distance between openings 1701 and 1705 does not equal the distance between openings 1701 and 1706.

Figure 18:
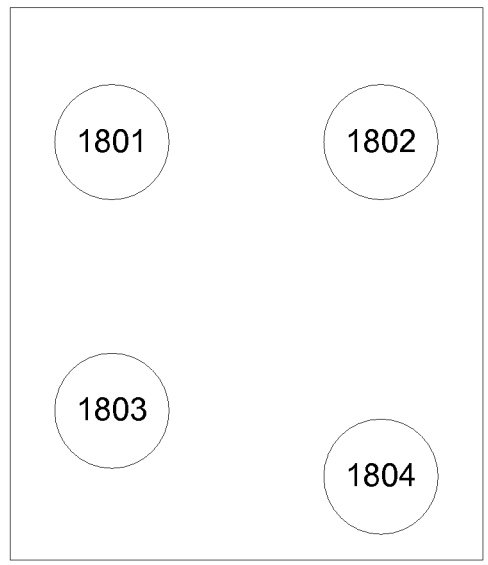
FIG. 18 shows another sensor opening pattern where one sensor opening is aligned asymmetrically with respect to the other sensor openings.

FIG. 18 shows a specific implementation of a sensor unit which is arranged to include four openings 1801-1804. Openings 1801 and 1802 are arranged in a line closer to a first edge of the sensor, while openings 1803 and 1804 are arranged closer to a second edge, which is opposite the first edge. In fact, opening 1804 is closer than opening 1803 to the second edge. In an implementation the first edge is distal to the second edge, which is closer to a cable attached to the probe or hand holding the probe.

In one implementation, openings 1801 and 1802 are detectors and openings 1803 and 1804 are sources. However, in other implementations, there can be one or more detectors, two or more detectors, one or more sources, or two or more sources. For example, there may be three detectors and one source or one detector and three sources.

In FIG. 18, the openings are positioned asymmetrically such that a line drawn through openings 1801 and 1802 is not parallel to a line through openings 1803 and 1804. However, a line drawn through openings 1801 and 1803 is parallel to a line through openings 1802 and 1804.

Additionally, the distance between openings 1801 and 1802 is shorter than the distance between openings 1803 and 1804. Thus, in FIG. 18, the distance between openings 1801 and 1803 does not equal the distance between openings 1802 and 1804 and the distance between openings 1802 and 1803 does not equal that between openings 1802 and 1804.

Figure 19:
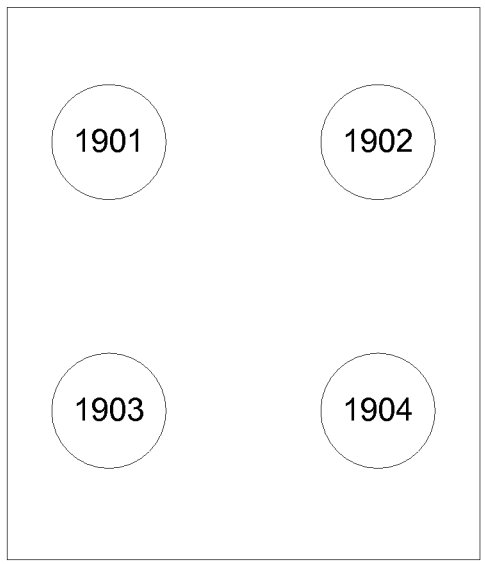
FIG. 19 shows a sensor opening pattern where the openings are arranged symmetrically about horizontal and vertical axes.

FIG. 19 shows a variation of the implementation of the sensor unit shown in FIG. 18. The sensor unit of this implementation also includes four openings 1901-1904. Openings 1901 and 1902 are arranged in a line closer to a first edge of the sensor, while openings 1903 and 1904 are arranged closer to a second edge, which is opposite the first edge. In one implementation, openings 1901 and 1902 are detectors and openings 1903 and 1904 are sources.

In FIG. 19, the openings are positioned symmetrically such that a line drawn through openings 1901 and 1902 is parallel, and equal, to a line through openings 1903 and 1904. Additionally, a line drawn through openings 1901 and 1903 is parallel, and equal, to a line through openings 1902 and 1904.

In an implementation, the distances between openings 1901-1902, 1902-1904, 1904-1903, and 1903-1901 are all equal; thus, in this implementation openings 1901, 1902, 1903, and 1904 form the vertices of a square. In other implementations, however, four openings may form the vertices of any quadrilateral, such as a rectangle, a rhombus, a trapezoid, or a parallelogram.

Some of the distances between the centers of particular openings are unequal; for instance, the distance between openings 1901 and 1903 does not equal the distance between openings 1901 and 1904.

Figure 20:
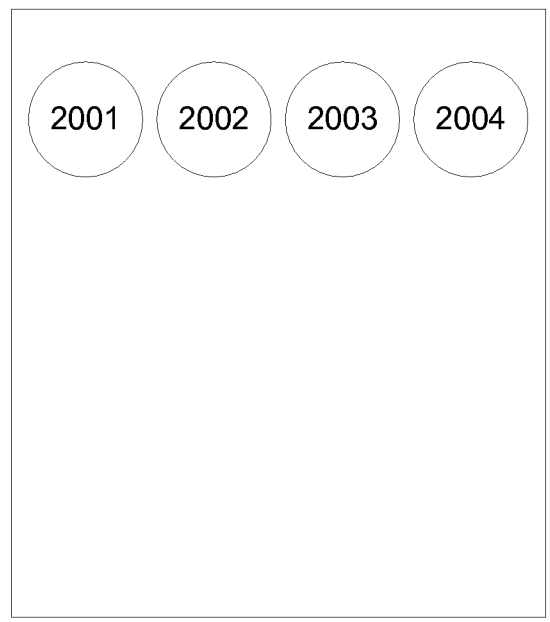
FIG. 20 shows a sensor opening pattern where the openings are aligned in a row.

FIG. 20 shows another variation of the implementation of the sensor unit shown in FIG. 18. Similar to FIGS. 18 and 19, this specific implementation of a sensor unit includes four openings 2001-2004.

However, in this variation, all four of the openings are arranged in a line closer to a first edge of the sensor. Specifically, in this figure, openings 2001-2004 lie in a row parallel to the first edge so that a straight line may be drawn through each opening. In one implementation, openings 2001 and 2002 are detectors and openings 2003 and 2004 are sources.

In this specific implementation, the distance between openings 2001 and 2002 is equal to the distance between openings 2002 and 2003; this distance is also equal to that between openings 2003 and 2004.

Additionally, the distance between openings 2001 and 2003 equals that between openings 2002 and 2004. In fact, this distance is twice the distance between each individual opening. Thus, the distance between openings 2001 and 2003 does not equal that between openings 2001 and 2002; the former is twice the distance of the latter.

Figure 21:
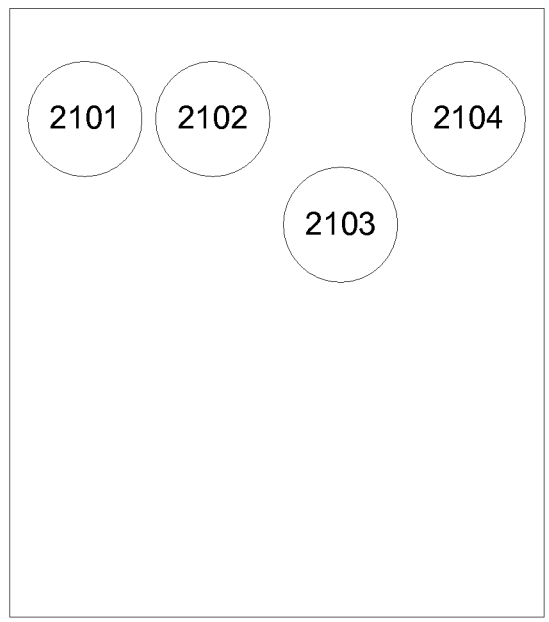
FIG. 21 shows a sensor opening pattern where the openings are aligned in a row, except for one of the openings.

FIG. 21 shows a variation of the implementation of the sensor unit shown in FIG. 20. This implementation of a sensor unit is similarly arranged to include four openings 2101-2104. Also, this arrangement of openings is located closer to a first edge of the sensor. However, in this figure, openings 2101, 2102, and 2104 lie in a row parallel to the first edge so that a straight line may be drawn through the center of each opening, while opening 2103 lies below that straight line.

In this implementation, opening 2103 lies equally spaced between openings 2102 and 2104; in other implementations, opening 2103 can lie closer to one opening than another. In one implementation, openings 2101 and 2102 are detectors and openings 2103 and 2104 are sources.

In this specific implementation, as mentioned above, the distance between openings 2102 and 2103 equals that between openings 2103 and 2104. Aside from this equality, the distances between the openings are unequal. For example, in this implementation, the distance between openings 2101 and 2103 does not equal the distance between openings 2102 and 2104 and the distance between openings 2102 and 2103 does not equal that between openings 2102 and 2104.

Figure 22:
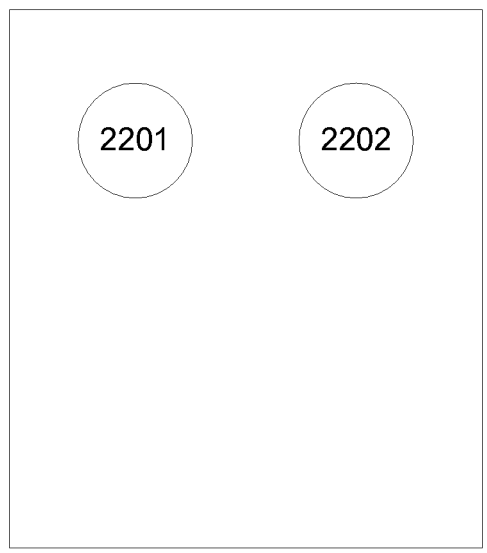
FIG. 22 shows a sensor opening pattern with two openings.

FIG. 22 shows a specific implementation of a sensor unit which is arranged to include two openings 2201 and 2202. Similar to FIGS. 20 and 21, this arrangement of openings is located closer to a first edge of the sensor. Additionally, openings 2201 and 2202 lie in a row parallel to the first edge so that a straight line may be drawn through each opening. In one implementation, opening 2201 is a detector and opening 2202 is a source.

Although we have shown sensor units with two, four, and six openings in these figures, other implementations may include different numbers of sensor openings. For instance, there may be three, five, seven, eight, or more openings.

Further, there may be any combination of detectors and sources and the number of detectors need not equal the number of sources. For instance, if there are three openings, there may be one detector and two sources or two detectors and one source. As another example, if there are eight openings, there may be two detectors and six sources, five detectors and three sources, or four detectors and four sources.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A probe for a medical device comprising:
   a cable interface, the cable interface being adapted to allow the probe to be coupled to a first radiation emitter and a first photodetector, wherein the first radiation emitter and the first photodetector are external to the probe;
   a sensor unit comprising a first source structure and a first detector structure, the first source structure being arranged to be coupled to the first radiation emitter via the cable interface, the first detector structure being arranged to be coupled to the first photodetector via the cable interface; and
   a marking mechanism output, positioned closer to the first detector structure than the cable interface.

2. The device of claim 1 wherein the sensor unit comprises a second source structure and a second detector structure, the second source structure being arranged to be coupled to a second radiation emitter via the cable interface, and the second detector structure being arranged to be coupled to a second photodetector via the cable interface, wherein the second radiation emitter and the second photodetector are external to the probe.

3. The device of claim 2 wherein a first distance is between the first source structure and the first detector structure, a second distance is between the first source structure and the second detector structure, a third distance is between the second source structure and the first detector structure, a fourth distance is between the second source structure and the second detector structure, and
   the first distance is not equal to the fourth distance and the second distance is not equal to the third distance.

4. The probe of claim 1 wherein the marking mechanism output comprises an ink nozzle.

5. The probe of claim 1 wherein the marking mechanism output is positioned within ten millimeters of the first detector structure.

6. The probe of claim 1 wherein the marking mechanism output is coupled to the sensor unit.

7. The probe of claim 1 comprising:
   a handle, wherein the sensor unit is coupled to the handle; and
   a light emitting diode, coupled to a handle.

8. The probe of claim 7 wherein the marking mechanism output is coupled to the handle.

9. A probe of a medical device comprising:
   a first retaining mechanism, to couple an oximeter sensor to the probe, wherein the oximeter sensor comprises a first source structure and a first detector structure;
   a first marking reservoir;

a second retaining mechanism, to couple the first marking reservoir to the probe; and a marking mechanism, coupled to the first marking reservoir.

10. The probe of claim 9 wherein the second retaining mechanism removably couples the first marking reservoir to the probe.

11. The probe of claim 9 wherein the second retaining mechanism is internal to the probe.

12. The probe of claim 9 wherein the first marking reservoir comprises a transparent window.

13. The probe of claim 9 comprises:
an elongated handle, wherein the first marking reservoir, the second retaining mechanism, and the marking mechanism are coupled to the handle.

14. The probe of claim 9 wherein the oximeter sensor comprises a second source structure and a second detector structure.

15. The probe of claim 9 comprising:
a second marking reservoir; and
a third retaining mechanism, to couple the second marking reservoir to the probe,
wherein the marking mechanism is coupled to the second marking reservoir.

16. The probe of claim 15 wherein the first marking reservoir comprises a first ink of a first color, and
the second marking reservoir comprises a second ink of a second color, different from the first.

17. The probe of claim 9 wherein the marking mechanism marks a tissue surface by placing ink on the tissue surface.

18. A probe of a medical device comprising:
a first retaining mechanism, to couple an oximeter sensor to the probe, wherein the oximeter sensor comprises a first source structure and a first detector structure;
a first marking reservoir;
a second retaining mechanism, to couple the first marking reservoir to the probe; and
a marking mechanism, coupled to the first marking reservoir,
wherein the first marking reservoir comprises a first ink of a first color and the probe further comprises:
a second marking reservoir comprising a second ink of a second color, different from the first, wherein the second marking source is coupled to the marking mechanism; and
a third retaining mechanism to couple the second marking reservoir to the probe.

19. The probe of claim 18 wherein the oximeter sensor comprises a second source structure and a second detector structure.

20. A probe of a medical device comprising:
a first retaining mechanism, to couple an oximeter sensor to the probe;
a first marking reservoir;
a second retaining mechanism, to couple the first marking reservoir to the probe; and
a marking mechanism, coupled to the first marking reservoir,
wherein the first marking reservoir comprises a first ink of a first color and the probe further comprises:
a second marking reservoir comprising a second ink of a second color, different from the first, wherein the second marking source is coupled to the marking mechanism and a third retaining mechanism to couple the second marking reservoir to the probe, wherein the oximeter sensor comprises a first source structure and a first detector structure and the probe comprises:
a first radiation emitter coupled to the first source structure; and
a first photodetector coupled to the first detector structure.

21. A probe of a medical device comprising:
a first retaining mechanism, to couple an oximeter sensor to the probe;
a first marking reservoir;
a second retaining mechanism, to couple the first marking reservoir to the probe;
a marking mechanism, coupled to the first marking reservoir; and
a cable interface, the cable interface being adapted to allow the probe to be coupled to a first radiation emitter and a first photodetector, wherein the first radiation emitter and the first photodetector are external to the probe.

22. A probe comprising:
a first retaining mechanism, to couple an oximeter sensor to the probe, wherein the oximeter sensor comprises a first source structure and a first detector structure;
a first marking reservoir;
a second retaining mechanism, to couple the first marking reservoir to the probe;
a marking mechanism, coupled to the first marking reservoir;
a first radiation emitter coupled to the first source structure;
a first photodetector coupled to the first detector structure; and
a handle, wherein the oximeter sensor is coupled to the handle via the first retaining mechanism, and the marking mechanism is coupled to the handle via the second retaining mechanism.

23. The probe of claim 22 wherein the first and second retaining mechanisms are combined into a single mechanism.

24. The probe of claim 22 wherein the marking mechanism comprises a first marking color output and a second color output, wherein the first marking color output is a different color from the second color output.

25. A probe of a medical device comprising:
a first retaining mechanism, to couple an oximeter sensor to the probe;
a first marking reservoir;
a second retaining mechanism, to couple the first marking reservoir to the probe; and
a marking mechanism, coupled to the first marking reservoir, wherein the oximeter sensor comprises a first source structure and a first detector structure and the probe comprises:
a first radiation emitter coupled to the first source structure; and
a first photodetector coupled to the first detector structure.

26. A probe of a medical device comprising:
a first retaining mechanism, to couple an oximeter sensor to the probe;
a first marking reservoir;
a second retaining mechanism, to couple the first marking reservoir to the probe; and
a marking mechanism, coupled to the first marking reservoir,
wherein the first marking reservoir comprises a first ink of a first color and the probe further comprises:
a second marking reservoir comprising a second ink of a second color, different from the first, wherein the second marking source is coupled to the marking mechanism;

a third retaining mechanism to couple the second marking reservoir to the probe; and a cable interface, the cable interface being adapted to allow the probe to be coupled to a first radiation emitter and a first photodetector, wherein the first radiation emitter and the first photodetector are external to the probe.

* * * * *